United States Patent
Do et al.

(10) Patent No.: US 8,685,178 B2
(45) Date of Patent: Apr. 1, 2014

(54) METHODS OF PREPARING METAL-MODIFIED SILICA NANOPARTICLES

(75) Inventors: Bao Trong Do, Decatur, GA (US); Thomas David Ehlert, Neenah, WI (US); Robert Allen Janssen, Alpharetta, GA (US); John Gavin MacDonald, Decatur, GA (US); Paul Warren Rasmussen, Nennah, WI (US); Shiming Zhuang, Menasha, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 871 days.

(21) Appl. No.: 12/335,176

(22) Filed: Dec. 15, 2008

(65) Prior Publication Data

US 2010/0150859 A1   Jun. 17, 2010

(51) Int. Cl.
*B06B 3/00* (2006.01)
*B22F 9/16* (2006.01)

(52) U.S. Cl.
USPC .......... 148/239; 75/345; 264/430; 264/442; 148/558

(58) Field of Classification Search
None
See application file for complete search history.

(56) References Cited

U.S. PATENT DOCUMENTS

| | | | |
|---|---|---|---|
| 2,115,056 | A | 4/1938 | Samuel |
| 2,307,206 | A | 1/1943 | Fischer |
| 2,584,053 | A | 1/1952 | Seavey et al. |
| 2,615,692 | A | 10/1952 | Muller |
| 2,620,894 | A | 12/1952 | Peterson et al. |
| 2,661,192 | A | 12/1953 | Horsley et al. |
| 2,946,981 | A | 7/1960 | O'Neill |
| 3,066,232 | A | 11/1962 | Branson, N. |
| 3,160,138 | A | 12/1964 | Platzman |
| 3,202,281 | A | 8/1965 | Weston |

(Continued)

FOREIGN PATENT DOCUMENTS

| | | |
|---|---|---|
| CA | 2175065 | 5/1995 |
| CH | 657067 | 8/1986 |

(Continued)

OTHER PUBLICATIONS

Non-final Office Action submitted in U.S. Appl. No. 12/704,058 dated Dec. 9, 2010.

(Continued)

*Primary Examiner* — George Wyszomierski
(74) *Attorney, Agent, or Firm* — Armstrong Teasdale LLP

(57) ABSTRACT

A method of preparing metal-modified silica particles is disclosed. Specifically, a treatment chamber is provided in which a first and a second formulation are ultrasonically mixed to prepare metal-modified silica particles. The treatment chamber has an elongate housing through which the first and second formulations flow longitudinally from a first inlet port and a second inlet port, respectively, to an outlet port thereof. An elongate ultrasonic waveguide assembly extends within the housing and is operable at a predetermined ultrasonic frequency to ultrasonically energize the formulations within the housing. An elongate ultrasonic horn of the waveguide assembly is disposed at least in part intermediate the inlet and outlet ports, and has a plurality of discrete agitating members in contact with and extending transversely outward from the horn intermediate the inlet and outlet ports in longitudinally spaced relationship with each other. The horn and agitating members are constructed and arranged for dynamic motion of the agitating members relative to the horn at the predetermined frequency and to operate in an ultrasonic cavitation mode of the agitating members corresponding to the predetermined frequency and the formulations being mixed in the chamber.

14 Claims, 12 Drawing Sheets

(56) References Cited

U.S. PATENT DOCUMENTS

Figure 1:
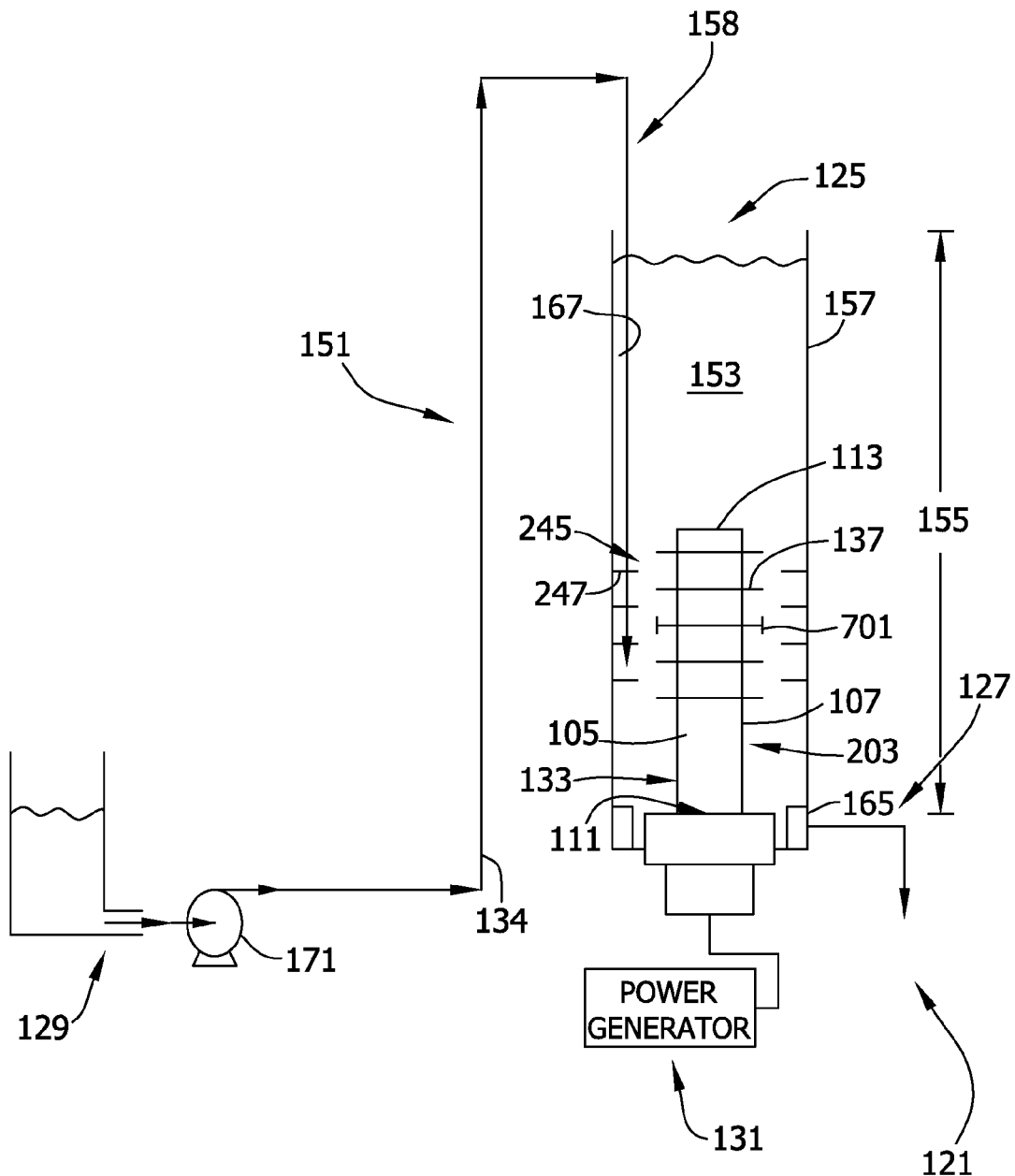

| | | |
|---|---|---|
| 3,239,998 A | 3/1966 | Carter et al. |
| 3,246,881 A | 4/1966 | Davidson et al. |
| 3,249,453 A | 5/1966 | Schnoring et al. |
| 3,273,631 A | 9/1966 | Neuman |
| 3,275,787 A | 9/1966 | Newberry |
| 3,278,165 A | 10/1966 | Gaffney |
| 3,284,991 A | 11/1966 | Ploeger et al. |
| 3,325,348 A | 6/1967 | Bennett |
| 3,326,470 A | 6/1967 | Loudin et al. |
| 3,338,992 A | 8/1967 | Kinney |
| 3,341,394 A | 9/1967 | Kinney |
| 3,425,951 A | 2/1969 | Ishiwata |
| 3,463,321 A | 8/1969 | VanIngen |
| 3,479,873 A | 11/1969 | Hermanns |
| 3,490,584 A | 1/1970 | Balamuth |
| 3,502,763 A | 3/1970 | Hartman |
| 3,519,251 A | 7/1970 | Hammitt et al. |
| 3,542,345 A | 11/1970 | Kuris |
| 3,542,615 A | 11/1970 | Dobo et al. |
| 3,567,185 A | 3/1971 | Ross et al. |
| 3,591,946 A | 7/1971 | Loe |
| 3,664,191 A | 5/1972 | Hermanns |
| 3,692,618 A | 9/1972 | Dorschner et al. |
| 3,782,547 A | 1/1974 | Dietert |
| 3,802,817 A | 4/1974 | Matsuki et al. |
| 3,865,350 A | 2/1975 | Burtis |
| 3,873,071 A | 3/1975 | Tatebe |
| 3,904,392 A | 9/1975 | VanIngen et al. |
| 4,035,151 A | 7/1977 | Czerny et al. |
| 4,062,768 A | 12/1977 | Elliot |
| 4,070,167 A | 1/1978 | Barbee et al. |
| 4,122,797 A | 10/1978 | Kawamura et al. |
| 4,168,295 A | 9/1979 | Sawyer |
| 4,218,221 A | 8/1980 | Cottell |
| 4,249,986 A | 2/1981 | Obeda |
| 4,259,021 A | 3/1981 | Goudy, Jr. |
| 4,260,389 A | 4/1981 | Lister |
| 4,266,879 A | 5/1981 | McFall |
| 4,340,563 A | 7/1982 | Appel et al. |
| 4,372,296 A | 2/1983 | Fahim |
| 4,398,925 A | 8/1983 | Trinh et al. |
| 4,425,718 A | 1/1984 | Kawaguchi |
| 4,511,254 A | 4/1985 | North et al. |
| 4,556,467 A | 12/1985 | Kuhn |
| 4,612,016 A | 9/1986 | Jaeger et al. |
| 4,612,018 A | 9/1986 | Tsuboi et al. |
| 4,663,220 A | 5/1987 | Wisneski et al. |
| 4,673,512 A | 6/1987 | Schram |
| 4,693,879 A | 9/1987 | Yoshimura et al. |
| 4,699,636 A | 10/1987 | Bofinger et al. |
| 4,706,509 A | 11/1987 | Riebel |
| 4,708,878 A | 11/1987 | Hagelauer et al. |
| 4,726,522 A | 2/1988 | Kokubo et al. |
| 4,743,361 A | 5/1988 | Schram |
| 4,848,159 A | 7/1989 | Kennedy et al. |
| 4,877,516 A | 10/1989 | Schram |
| 4,879,011 A | 11/1989 | Schram |
| 4,929,279 A | 5/1990 | Hays |
| RE33,524 E | 1/1991 | Schram |
| 4,983,045 A | 1/1991 | Taniguchi |
| 5,006,266 A | 4/1991 | Schram |
| 5,026,167 A | 6/1991 | Berliner, III |
| 5,032,027 A | 7/1991 | Berliner, III |
| 5,059,249 A | 10/1991 | Hays |
| 5,096,532 A | 3/1992 | Neuwirth et al. |
| 5,110,403 A | 5/1992 | Ehlert |
| 5,122,165 A | 6/1992 | Wang et al. |
| 5,164,094 A | 11/1992 | Stuckart |
| 5,169,067 A | 12/1992 | Matsusaka et al. |
| 5,242,557 A | 9/1993 | Jones et al. |
| 5,258,413 A | 11/1993 | Isayev |
| 5,269,297 A | 12/1993 | Weng et al. |
| 5,326,164 A | 7/1994 | Logan |
| 5,330,100 A | 7/1994 | Malinowski |
| 5,335,449 A | 8/1994 | Beatty |
| 5,372,634 A | 12/1994 | Monahan |
| 5,373,212 A | 12/1994 | Beau |
| 5,375,926 A | 12/1994 | Omasa |
| 5,391,000 A | 2/1995 | Taniguchi |
| 5,466,722 A | 11/1995 | Stoffer et al. |
| 5,519,670 A | 5/1996 | Walter |
| 5,536,921 A | 7/1996 | Hedrick et al. |
| 5,583,292 A | 12/1996 | Karbach et al. |
| 5,585,565 A | 12/1996 | Glascock et al. |
| 5,665,383 A | 9/1997 | Grinstaff et al. |
| 5,681,457 A | 10/1997 | Mahoney |
| 5,711,888 A | 1/1998 | Tramler et al. |
| 5,770,124 A | 6/1998 | Marecki et al. |
| 5,803,270 A | 9/1998 | Brodeur |
| 5,810,037 A | 9/1998 | Sasaki et al. |
| 5,831,166 A | 11/1998 | Kozuka et al. |
| 5,853,456 A | 12/1998 | Bryan et al. |
| 5,868,153 A | 2/1999 | Cohen et al. |
| 5,873,968 A | 2/1999 | Pike et al. |
| 5,902,489 A | 5/1999 | Yasuda et al. |
| 5,916,203 A | 6/1999 | Brandon et al. |
| 5,922,355 A | 7/1999 | Parikh et al. |
| 5,935,883 A | 8/1999 | Pike |
| 5,937,906 A | 8/1999 | Kozyuk |
| 5,964,926 A | 10/1999 | Cohen |
| 5,979,664 A | 11/1999 | Brodeur |
| 6,010,592 A | 1/2000 | Jameson et al. |
| 6,020,277 A | 2/2000 | Jameson |
| 6,035,897 A | 3/2000 | Kozyuk |
| 6,053,028 A | 4/2000 | Kraus, Jr. et al. |
| 6,053,424 A | 4/2000 | Gipson et al. |
| 6,055,859 A | 5/2000 | Kozuka et al. |
| 6,060,416 A | 5/2000 | Kobata et al. |
| 6,074,466 A | 6/2000 | Iwasa |
| 6,090,731 A | 7/2000 | Pike et al. |
| 6,106,590 A | 8/2000 | Ueno et al. |
| 6,169,045 B1 | 1/2001 | Pike et al. |
| 6,200,486 B1 | 3/2001 | Chahine et al. |
| 6,218,483 B1 | 4/2001 | Muthiah et al. |
| 6,221,258 B1 | 4/2001 | Feke et al. |
| 6,254,787 B1 | 7/2001 | Kimura et al. |
| 6,266,836 B1 | 7/2001 | Gallego Juarez et al. |
| 6,315,215 B1 | 11/2001 | Gipson et al. |
| 6,322,240 B1 | 11/2001 | Omasa |
| 6,332,541 B1 | 12/2001 | Coakley et al. |
| 6,361,697 B1 | 3/2002 | Coury et al. |
| 6,368,414 B1 | 4/2002 | Johnson |
| 6,380,264 B1 | 4/2002 | Jameson et al. |
| 6,383,301 B1 | 5/2002 | Bell et al. |
| 6,450,417 B1 | 9/2002 | Gipson et al. |
| 6,467,350 B1 | 10/2002 | Kaduchak et al. |
| 6,482,327 B1 | 11/2002 | Mori et al. |
| 6,506,584 B1 | 1/2003 | Chandler et al. |
| 6,547,903 B1 | 4/2003 | McNichols et al. |
| 6,547,935 B2 | 4/2003 | Scott |
| 6,547,951 B1 | 4/2003 | Maekawa |
| 6,551,607 B1 | 4/2003 | Minerath, III |
| 6,576,042 B2 | 6/2003 | Kraus et al. |
| 6,582,611 B1 | 6/2003 | Kerfoot |
| 6,593,436 B2 | 7/2003 | Austin et al. |
| 6,605,252 B2 | 8/2003 | Omasa |
| 6,617,588 B1 | 9/2003 | Sato |
| 6,620,226 B2 | 9/2003 | Hutton et al. |
| 6,624,100 B1 | 9/2003 | Pike et al. |
| 6,627,265 B2 | 9/2003 | Kutilek |
| 6,655,826 B1 | 12/2003 | Leanos |
| 6,659,365 B2 | 12/2003 | Gipson et al. |
| 6,676,003 B2 | 1/2004 | Ehlert et al. |
| 6,689,730 B2 | 2/2004 | Hortel et al. |
| 6,739,524 B2 | 5/2004 | Taylor-McCune et al. |
| 6,770,600 B1 | 8/2004 | Lamola |
| 6,817,541 B2 | 11/2004 | Sands et al. |
| 6,818,128 B2 | 11/2004 | Minter |
| 6,837,445 B1 | 1/2005 | Tsai |
| 6,841,921 B2 | 1/2005 | Stegelmann |
| 6,858,181 B2 | 2/2005 | Aoyagi |
| 6,878,288 B2 | 4/2005 | Scott |
| 6,883,724 B2 | 4/2005 | Adiga et al. |
| 6,890,593 B2 | 5/2005 | Tian |

(56) References Cited

U.S. PATENT DOCUMENTS

| | | |
|---|---|---|
| 6,897,628 B2 | 5/2005 | Gunnerman |
| 6,902,650 B2 | 6/2005 | Park et al. |
| 6,911,153 B2 | 6/2005 | Minter |
| 6,929,750 B2 | 8/2005 | Laurell et al. |
| 6,935,770 B2 | 8/2005 | Schueler |
| 6,936,151 B1 | 8/2005 | Lock |
| 7,018,546 B2 | 3/2006 | Kurihara et al. |
| 7,083,322 B2 | 8/2006 | Moore et al. |
| 7,083,764 B2 | 8/2006 | Scott |
| 7,090,391 B2 | 8/2006 | Taniguchi |
| 7,108,137 B2 | 9/2006 | Lal et al. |
| 7,150,779 B2 | 12/2006 | Meegan, Jr. |
| 7,156,201 B2 | 1/2007 | Peshkovskiy et al. |
| 7,293,909 B2 | 11/2007 | Taniguchi |
| 7,322,431 B2 | 1/2008 | Ratcliff |
| 7,338,551 B2 | 3/2008 | Kozyuk |
| 7,404,666 B2 | 7/2008 | Tessien |
| 7,414,009 B2 | 8/2008 | Tanaka et al. |
| 7,419,519 B2 | 9/2008 | Li et al. |
| 7,424,883 B2 | 9/2008 | McNichols et al. |
| 7,465,426 B2 | 12/2008 | Kerherve et al. |
| 7,504,075 B2 | 3/2009 | Marhasin |
| 7,516,664 B2 | 4/2009 | Meier et al. |
| 7,533,830 B1 | 5/2009 | Rose |
| 7,582,156 B2 | 9/2009 | Tanaka et al. |
| 7,673,516 B2 | 3/2010 | Janssen et al. |
| 7,703,698 B2* | 4/2010 | Janssen et al. ............ 239/102.2 |
| 7,712,353 B2 | 5/2010 | Janssen et al. |
| 7,735,751 B2 | 6/2010 | Ehlert et al. |
| 7,780,743 B2* | 8/2010 | Greaves et al. .................. 8/405 |
| 7,785,674 B2* | 8/2010 | Janssen et al. ................ 427/600 |
| 2001/0040935 A1 | 11/2001 | Case |
| 2002/0036173 A1 | 3/2002 | Feke et al. |
| 2002/0164274 A1 | 11/2002 | Haggett et al. |
| 2003/0042174 A1 | 3/2003 | Austin |
| 2003/0047067 A1 | 3/2003 | Kraus et al. |
| 2003/0048692 A1 | 3/2003 | Cohen et al. |
| 2003/0051989 A1 | 3/2003 | Austin |
| 2003/0061939 A1 | 4/2003 | Hutton et al. |
| 2003/0066899 A1 | 4/2003 | Gipson |
| 2003/0116014 A1 | 6/2003 | Possanza et al. |
| 2003/0143110 A1 | 7/2003 | Kritzler |
| 2003/0194692 A1 | 10/2003 | Purdum |
| 2003/0234173 A1 | 12/2003 | Minter |
| 2004/0022695 A1 | 2/2004 | Simon et al. |
| 2004/0065599 A1 | 4/2004 | Lal et al. |
| 2004/0079580 A1 | 4/2004 | Manna et al. |
| 2004/0120904 A1 | 6/2004 | Lye et al. |
| 2004/0142041 A1 | 7/2004 | MacDonald et al. |
| 2004/0187524 A1 | 9/2004 | Sen et al. |
| 2004/0202728 A1 | 10/2004 | Shanker et al. |
| 2005/0000914 A1 | 1/2005 | Dahlberg et al. |
| 2005/0008560 A1 | 1/2005 | Kataoka et al. |
| 2005/0017599 A1 | 1/2005 | Puskas |
| 2005/0025797 A1 | 2/2005 | Wang et al. |
| 2005/0042129 A1 | 2/2005 | Kazem |
| 2005/0082234 A1 | 4/2005 | Solenthaler |
| 2005/0084438 A1* | 4/2005 | Do et al. ................ 423/244.02 |
| 2005/0084464 A1 | 4/2005 | McGrath et al. |
| 2005/0085144 A1 | 4/2005 | MacDonald et al. |
| 2005/0092931 A1 | 5/2005 | Gadgil et al. |
| 2005/0094486 A1 | 5/2005 | Taniguchi |
| 2005/0129161 A1 | 6/2005 | Laberge |
| 2005/0207431 A1 | 9/2005 | Beca et al. |
| 2005/0208303 A1* | 9/2005 | Atarashi et al. ............... 428/403 |
| 2005/0220665 A1 | 10/2005 | Ding |
| 2005/0260106 A1 | 11/2005 | Marhasin |
| 2006/0000034 A1 | 1/2006 | McGrath |
| 2006/0008442 A1 | 1/2006 | MacDonald et al. |
| 2006/0120212 A1 | 6/2006 | Taniguchi et al. |
| 2007/0062801 A1 | 3/2007 | Foret |
| 2007/0114306 A1 | 5/2007 | Kawakami et al. |
| 2007/0119785 A1 | 5/2007 | Englehardt et al. |
| 2007/0131034 A1 | 6/2007 | Ehlert et al. |
| 2007/0170277 A1 | 7/2007 | Ehlert |
| 2008/0062811 A1* | 3/2008 | Janssen et al. ................. 366/127 |
| 2008/0063718 A1* | 3/2008 | Janssen et al. ................. 424/489 |
| 2008/0067418 A1 | 3/2008 | Ross |
| 2008/0069887 A1 | 3/2008 | Baran et al. |
| 2008/0117711 A1 | 5/2008 | Omasa |
| 2008/0155763 A1 | 7/2008 | Janssen et al. |
| 2008/0156737 A1 | 7/2008 | Janssen et al. |
| 2008/0159063 A1 | 7/2008 | Janssen et al. |
| 2008/0192568 A1 | 8/2008 | Hielscher et al. |
| 2008/0251375 A1 | 10/2008 | Hielscher et al. |
| 2009/0014377 A1 | 1/2009 | Janssen et al. |
| 2009/0147905 A1 | 6/2009 | Janssen et al. |
| 2009/0155091 A1 | 6/2009 | Ehlert et al. |
| 2009/0158936 A1 | 6/2009 | Janssen et al. |
| 2009/0162258 A1 | 6/2009 | Janssen et al. |
| 2009/0165654 A1 | 7/2009 | Koenig et al. |
| 2009/0166177 A1* | 7/2009 | Wenzel et al. ............ 204/157.62 |
| 2009/0168590 A1* | 7/2009 | Koenig et al. ................. 366/114 |
| 2009/0168591 A1* | 7/2009 | Wenzel et al. ................. 366/116 |
| 2009/0262597 A1 | 10/2009 | Kieffer et al. |
| 2010/0150859 A1 | 6/2010 | Do et al. |
| 2010/0206742 A1 | 8/2010 | Janssen et al. |
| 2010/0296975 A1 | 11/2010 | Peshkovsky et al. |

FOREIGN PATENT DOCUMENTS

| | | |
|---|---|---|
| CN | 1535249 A | 10/2004 |
| CN | 1247628 | 3/2006 |
| CN | 101153138 | 4/2008 |
| DD | 262553 A3 | 12/1988 |
| DE | 9017338 | 3/1991 |
| DE | 4444525 | 6/1996 |
| DE | 19618217 A1 | 11/1997 |
| DE | 19854013 | 5/2000 |
| DE | 19913397 | 9/2000 |
| DE | 19938254 | 2/2001 |
| DE | 10015144 A1 | 10/2001 |
| DE | 29825063 | 6/2004 |
| DE | 202005009923 U1 | 4/2005 |
| DE | 102004040233 | 3/2006 |
| DE | 102005025118 | 1/2007 |
| DE | 102005034629 | 1/2007 |
| EP | 0269941 A1 | 6/1988 |
| EP | 0292470 | 11/1988 |
| EP | 347891 | 12/1989 |
| EP | 0457187 A2 | 11/1991 |
| EP | 0459967 | 12/1991 |
| EP | 625482 | 11/1994 |
| EP | 648531 | 4/1995 |
| EP | 0894612 A2 | 2/1999 |
| EP | 1375432 A1 | 1/2004 |
| EP | 1954388 | 3/2007 |
| EP | 0983968 | 3/2008 |
| EP | 2173669 A2 | 4/2010 |
| EP | 2176173 A2 | 4/2010 |
| FR | 2793811 | 11/2000 |
| FR | 2832703 A1 | 5/2005 |
| GB | 1404575 | 9/1975 |
| JP | 56028221 | 3/1981 |
| JP | 57119853 | 7/1982 |
| JP | 5834051 | 2/1983 |
| JP | 62001413 A | 1/1987 |
| JP | 62039839 U | 3/1987 |
| JP | 6372364 | 4/1988 |
| JP | 63104664 | 5/1988 |
| JP | 1108081 | 4/1989 |
| JP | 2025602 | 1/1990 |
| JP | 02281185 A | 11/1990 |
| JP | 03053195 A | 3/1991 |
| JP | 3086258 | 4/1991 |
| JP | 03-157129 A | 5/1991 |
| JP | 6228824 | 8/1994 |
| JP | 8304388 | 11/1996 |
| JP | 9286943 | 11/1997 |
| JP | 10060331 | 3/1998 |
| JP | 11133661 | 5/1999 |
| JP | 2000158364 | 12/1999 |
| JP | 2001017970 | 1/2001 |
| JP | 2001252588 | 9/2001 |

(56) References Cited

FOREIGN PATENT DOCUMENTS

| | | |
|---|---|---|
| JP | 2003103152 A | 4/2003 |
| JP | 2004020176 | 1/2004 |
| JP | 2004256783 | 9/2004 |
| JP | 2005118688 | 5/2005 |
| JP | 2000024494 A | 1/2010 |
| KR | 20020073778 A | 9/2002 |
| KR | 1020050013858 A | 2/2005 |
| KR | 1020050113356 A | 12/2005 |
| SU | 203582 A | 1/1967 |
| WO | 9400757 | 1/1994 |
| WO | 9420833 | 9/1994 |
| WO | 9429873 A | 12/1994 |
| WO | 9600318 | 1/1996 |
| WO | 9609112 A1 | 3/1996 |
| WO | 9620017 A1 | 7/1996 |
| WO | 9743026 | 11/1997 |
| WO | 9817373 | 4/1998 |
| WO | 9844058 | 10/1998 |
| WO | 9933520 | 7/1999 |
| WO | 0004978 | 2/2000 |
| WO | 0041794 | 7/2000 |
| WO | 0139200 A | 5/2001 |
| WO | 0222252 | 3/2002 |
| WO | 0250511 | 6/2002 |
| WO | 0280668 A2 | 10/2002 |
| WO | 03012800 | 2/2003 |
| WO | 03102737 | 12/2003 |
| WO | 2004026452 | 4/2004 |
| WO | 2004064487 | 8/2004 |
| WO | 2005011804 | 2/2005 |
| WO | 2005014489 A1 | 2/2005 |
| WO | 2006037591 | 4/2006 |
| WO | 2006043970 A2 | 4/2006 |
| WO | 2006073645 A1 | 7/2006 |
| WO | 2006074921 | 7/2006 |
| WO | 2006093804 | 9/2006 |
| WO | 2007011520 A2 | 1/2007 |
| WO | 2007060245 A1 | 5/2007 |
| WO | 2007095871 | 8/2007 |
| WO | 2008029379 | 3/2008 |
| WO | 2008047259 | 4/2008 |
| WO | 2008085806 | 7/2008 |

OTHER PUBLICATIONS

Non-final Office Action submitted in U.S. Appl. No. 11/530,183 dated Oct. 13, 2010.
Final Office action issued in U.S. Appl. No. 11/966,447 mailed Jan. 5, 2011.
Supplementary European Search Report issued in EP Application No. 08789242 mailed Dec. 17, 2010.
International Search Report and Written Opinion regarding PCT/IB2007/052947, dated Mar. 12, 2008.
U.S. Appl. No. 11/777,145, filed Jul. 12, 2007.
U.S. Appl. No. 11/777,151, filed Jul. 12, 2007.
International Search Report and Written Opinion regarding PCT/IB2007/052945, dated Feb. 1, 2008.
International Search Report and Written Opinion regarding PCT/IB2007/052988, 4 pages, dated Feb. 14, 2008.
U.S. Appl. No. 11/777,140, filed Jul. 12, 2007.
Taleyarkhan, et al., "Evidence for Nuclear Emissions During Acoustic Cavitation," Science, (Mar. 8, 2002), vol. 295, pp. 1868-1873.
Kloeppel, James E., "Temperature inside collapsing bubble four times that of sun," News Bureau, University of Illinois at Urbana-Champaign.
Tal-Figiel B., The Formation of Stable W/O,O/W, W/O/W Cosmetic Emulsions in an Ultrasonic Field, viewed at http://www.atypon-link.com/ICHEME/doi/abs/10.1205/cherd06199 on Oct. 19, 2007.
"Controlled Thermonuclear Fusion," viewed at http://library.thinkquest.org/17940/texts/fusion_controlled/fusion_controlled.html on Oct. 23, 2007.
Flannigan, "Measurement of Pressure and Density Inside a Single Sonoluminescing Bubble," Physical Review Letters (May 26, 2006), PRL 96.
Taleyarkhan, et al., "Additional Evidence of Nuclear Emissions During Acoustic Cavitation," Physcial Review E, (Mar. 2004). vol. 69.
"Thermonuclear Fusion Energy Source for Future Generations," viewed at http://www.crppwww.epfl.ch/crppfusion/ on Oct. 23, 2007.
Peplow, Mark, "Desktop fusion is back on the table," viewed at http://nature.com/news/2006/060109/full/060109-5.html on May 4, 2007.
Lahey, Taleyarkhan, and Nigmatulin, "Bubble Power," IEEE spectrum, May 2005, pp. 39-43.
U.S. Appl. No. 11/963,237, filed Dec. 21, 2007.
International Search Report regarding PCT/IB2007/053622, dated Feb. 14, 2008.
International Search Report and Written Opinion regarding PCT/IB2007/053623, dated Feb. 14, 2008.
International Search Report and Written Opinion regarding PCT/IB2007/053621, dated Feb. 14, 2008.
International Search Report and Written Opinion regarding PCT/IB2007/054892, dated May 15, 2008.
International Search Report and Written Opinion regarding PCT/IB2007/054898, dated May 15, 2008.
Non-final office action regarding U.S. Appl. No. 11/530,311, dated Nov. 5, 2008.
Non-final Office Action issued in U.S. Appl. No. 11/777,151 mailed Dec. 8, 2010.
Final Office Action issued in U.S. Appl. No. 11/966,418 mailed Jan. 12, 2011.
Non-final Office action issued in U.S. Appl. No. 11/963,139, dated Feb. 18, 2011.
Non-final Office action issued in U.S. Appl. No. 11/777,140, dated Feb. 23, 2011.
International Search Report and Written Opinion regarding PCT/IB2008/052760, dated Feb. 17, 2009.
International Search Report and Written Opinion, PCT/IB2008/055051 (Feb. 20, 2009).
International Search Report and Written Opinion for PCT/IB2008/052764 mailed Apr. 2, 2009.
Final Office Action issued in U.S. Appl. No. 11/966,458, dated Mar. 17, 2011.
Final Office Action issued in U.S. Appl. No. 11/530,183, dated Mar. 22, 2011.
Non-Final Office Action issued in U.S. Appl. No. 11/966,472, dated Mar. 31, 2011.
Final Office Action issued in U.S. Appl. No. 12/335,231, dated Mar. 31, 2011.
Barbaglia et al., "Search of Fusion Reactions During the Cavitation of a Single Bubble in Deuterated Liquids," Physica Scripta 72, pp. 75-78 (2005).
International Search Report and Written Opinion from PCT/IB2008/052766, dated Mar. 31, 2009.
Non-final office action regarding U.S. Appl. No. 11/617,515, dated Mar. 27, 2009.
Non-final Office action regarding U.S. Appl. No. 11/965,435, dated Mar. 11, 2010.
English translation of Nagel WO 2006/074921 A1, accessed on the EPO website, Jul. 20, 2006.
Non-final office action regarding U.S. Appl. No. 11/950,943, dated May 1, 2009.
J.D. Lawson, "Some Criteria for a Power Producing Thermonuclear Reactor", Proc. Phys. Soc. B70, pp. 6-10 (1957).
L.A. Artsimovich, "Controlled Thermonuclear Reactions", Gordon and Breach Science Publishers, New York, first English translation, 1964.
D.R.O. Morrison, "Cold Fusion Update No. 9", Jan. 1994, from Newsgroups sci.physics.fusion, http://www.groups.google.com.
Brenner et al, Single-bubble sonoluminescence, Reviews of Modern Physics, vol. 74, Apr. 2002, pp. 425-484.
J. Lister, Plasma Physics and Controlled Fusion 48, pp. 715-716 (2006).
U.S. Department of Energy, "Report of the Review of Low Energy Nuclear Reactions", Dec. 1, 2004 (USDOE).
Final Office Action Regarding U.S. Appl. No. 11/530,311 dated Jun. 23, 2009.

(56) References Cited

OTHER PUBLICATIONS

Takehi Moriguchi, et al. "Metal-modified silica adsorbents for removal of humic substances in water." Journal of Colloid and Interface Science 283, 2005 300-310, See Abstract, pp. 301 and 304.
International Search Report and Written Opinion regarding PCT/IB2009/055090, dated Jul. 16, 2010.
International Search Report and Written Opinion regarding PCT/IB2009/055092, dated Jul. 16, 2010.
Non-final office action regarding U.S. Appl. No. 11/617,497, dated Jun. 26, 2009.
International Search Report and Written Opinion regarding PCT/IB2008/055396, dated Jul. 29, 2009.
Non-final Office action regarding U.S. Appl. No. 11/963,237, dated Jul. 8, 2010.
Non-final Office action issued in related U.S. Appl. No. 11/777,140 on Aug. 9, 2010.
Non-Final Office action issued in related U.S. Appl. No. 11/966,418 on Aug. 2, 2010.
Non-Final Office action issued in related U.S. Appl. No. 11/966,447 on Aug. 2, 2010.
International Search Report and Written Opinion issued Aug. 18, 2009 for PCT/IB2008/055520.
International Search Report and Written Opinion issued Aug. 18, 2009 for PCT/IB2008/055517.
International Search Report and Written Opinion issued Aug. 18, 2009 for PCT/IB2008/055518.
International Search Report and Written Opinion regarding PCT/IB2008/055514, dated Aug. 25, 2009.
International Search Report and Written Opinion regarding PCT/IB2008/055395, dated Sep. 14, 2009.
International Search Report and Written Opinion regarding PCT/IB2008/055394, dated Sep. 28, 2009.
Blume, T. and Neis, U. "Improved wastewater disinfection by ultrasonic pre-treatment." Ultrasonics Sonochemistry, 2004, No. 11, pp. 333-336.
European Office Action regarding European Application No. 07805228.9, dated Oct. 9, 2009.
Oct. 27, 2010 Letter regarding the Office action issued for Mexican Patent Application No. MX/a/2009/002519 mailed Oct. 12, 2010.
Kuo et al., "Nano-particles dispersion effect on Ni/Al2O3 Composite Coatings," Materials Chemistry and Physics, 86: 5-10 (2004).
Sivakumar et al., "Preparation of nanosized TiO2 supported on activated alumina by a sonochemical method: observation of an increased photocatalytic decolourisation efficiency," Research on Chemical Intermediates, 30(7-8): 785-792 (2004).
Non-final Office action issued in related U.S. Appl. No. 11/530,210 on Jun. 28, 2010.
Non-final Office action issued in related U.S. Appl. No. 11/530,210 on Dec. 1, 2010.
Final Office action issued in related U.S. Appl. No. 11/777,140 Dec. 1, 2010.
Non-final Office Action received in U.S. Appl. No. 11/966,458 mailed Sep. 28, 2010.
Non-final Office Action regarding U.S. Appl. No. 12/335,231, dated Oct. 15, 2009.
Non-final Office action regarding U.S. Appl. No. 11/530,183, dated Apr. 19, 2010.
First Office Action for China Patent Application No. 200880121407.2, dated Aug. 24, 2011.
First Office Action for China Patent Application No. 200780033331.3, dated Nov. 14, 2011.
Final Office Action issued for U.S. Appl. No. 11/530,210 mailed Apr. 19, 2011.
First Office Action for China Patent Application No. 200880016947.3, dated Jun. 24, 2011.
First Office Action for Russian Patent Application No. 2009112526, dated Apr. 28, 2011.
Final Office Action issued for U.S. Appl. No. 11/530,210, mailed Jul. 1, 2011.
Non-Final Office Action issued for U.S. Appl. No. 12/335,231, mailed Jul. 13, 2011.
Non-Final Office Action issued for U.S. Appl. No. 11/963,139, mailed Jun. 15, 2011.
Non-final Office Action received in U.S. Appl. No. 12/438,317, mailed Sep. 24, 2012.
Chinese First Office Action for Patent Application No. 200880123165.0 dated Oct. 10, 2012; 9 pages.
Chinese Office Action for Patent Application No. 200880123174.X dated Mar. 27, 2013; 5 pages.
Extended European Search Report received in EP Patent Application No. 08868425 dated Feb. 14, 2012.
Chinese First Office Action for Patent Application No. 200880123174.X dated Sep. 20, 2012; 8 pages.
Chinese First Office Action for Patent Application No. 200880123172.0 dated Oct. 10, 2012; 9 pages.
EP Office Action for Patent Application No. 08 789 246.9-2104 dated Sep. 4, 2012; 4 pages.
EP Office Action for Patent Application No. 08 789 248.5-2104 dated Sep. 4, 2012; 4 pages.
Extended European Search Report for EP Patent Application No. 08867871.9, mailed Sep. 27, 2012.
Extended European Search Report received in EP Patent Application No. 08789248.5 dated Nov. 30, 2011.
Extended European Search Report regarding European Application No. 13159386.5, dated May 3, 2013; 8 pages.
European Search Report regarding European Application No. 08789248.5, dated May 2, 2013; 3 pages.
Non-Final Office Action for U.S. Appl. No. 11/530,210 dated Jul. 17, 2013; 14 pages.

\* cited by examiner

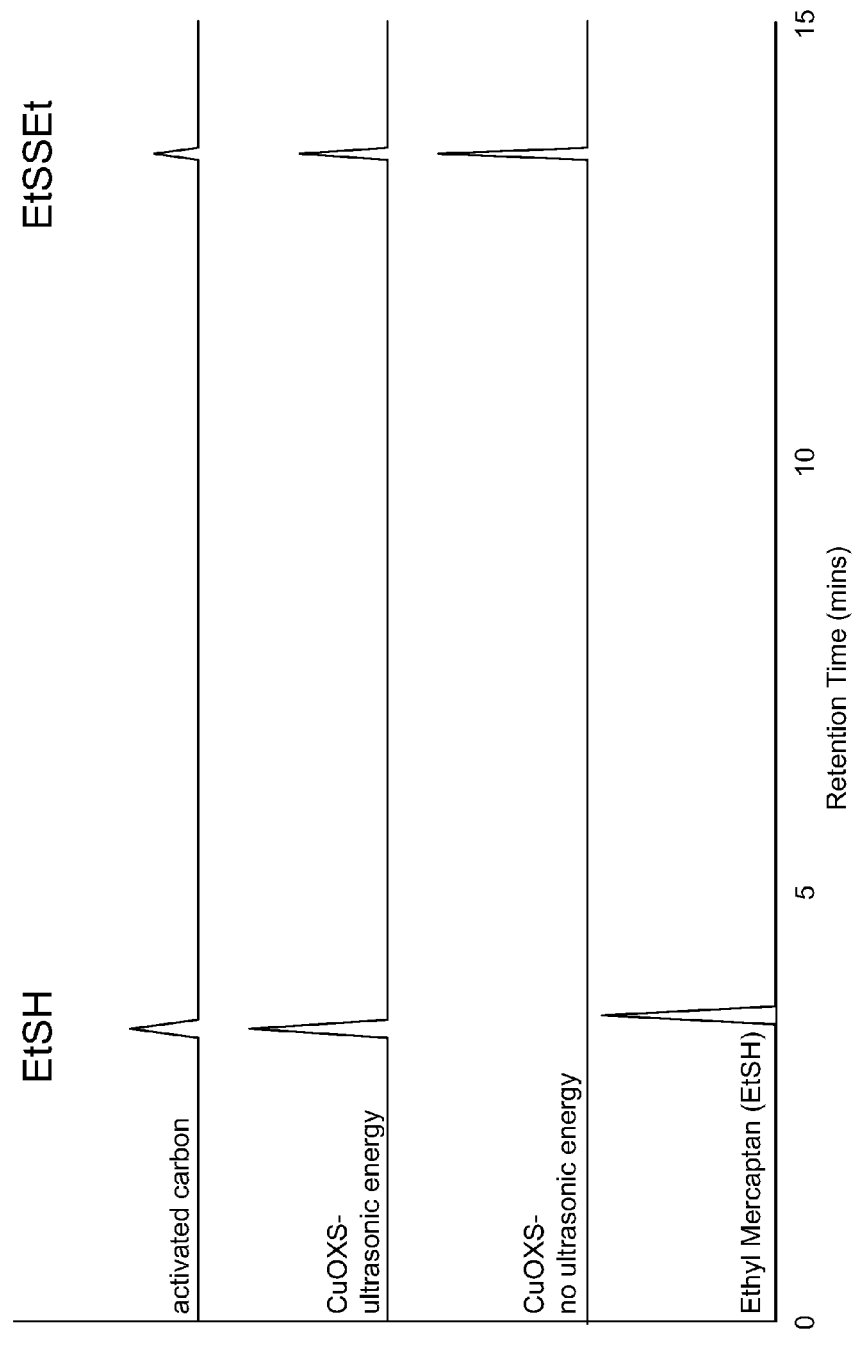

METHODS OF PREPARING METAL-MODIFIED SILICA NANOPARTICLES

FIELD OF DISCLOSURE

The present disclosure relates generally to methods for preparing metal-modified silica nano-particles. More particularly, methods for ultrasonically mixing a first and second formulation using an ultrasonic mixing system to prepare metal-modified silica particles are disclosed.

BACKGROUND OF DISCLOSURE

At least some known currently used odor control technologies are prepared by chemically depositing transition metal layers onto the surface of silica nano-particles. For instance, U.S. Patent Pub. No, 2005/0084438 to Do, et al., describes modifying the surface of silica particles with a transition metal so that the silica particles are bonded to the transition metal through a covalent or coordinate bond. Further, U.S. Patent Pub. No. 2006/0008442 to MacDonald, et al. describes modified nano-particles that have active sites that bind various gases and/or odorous compounds, thereby removing these compounds from a medium such as air or water. The metal ions are absorbed onto the surface of the nano-particle and bound strongly to the surface. These modified nano-particles may be applied to nonwoven webs to provide odor removing articles for industrial and consumer use. Although these modified nano-particles are useful, current procedures for forming these nano-particles have multiple problems, which can waste time, energy, and money for manufacturers of these modified nano-particles.

Specifically, synthesis of this technology is sensitive to reagent concentration, as aggregation and gelation in the reaction suspension may be observed at silica nano-particle concentrations above 4% (wt/wt). With this constraint, manufacturing and processing of the technology at the production scale entails higher costs due to more energy expensed to remove higher volumes of solvent. Additionally, more substrate material is needed in order to incorporate higher loading of technology into the product for increased odor removal efficacy. Particle agglomeration, also referred to herein as gelation, may be driven by a strong ionic strength nature in the reaction media due to the chemicals in that media.

Further, modified nano-particles formed by a stirred suspension of silica particles and copper salts with a base that is slowly added results in the active metal complex being formed on the surface of the silica in discrete zones or nodes. It has been discovered that the modified nano-particles formed by this method are capable of converting, for example, thiols (mercaptans) odors into disulphides. The human nose is particularly sensitive to these odors and can detect the presence of thiol odors down to part-per-billion (ppb). The human nose's ability to detect disulphides, however, is significantly less, in fact around tens of parts-per-million (ppm). Thus, the modified nano-particles may convert the malodor into a compound that can only be detected at significantly higher levels and therefore effectively converts the odor into something the human nose cannot detect. The modified nano-particles could perform this catalytic conversion continuously for an extended period of time.

Once the modified nano-particles are formed, three major mechanisms are involved in remediation of odor compounds: (1) physical adsorption; (2) catalysis; and (3) chemical absorption. Physical adsorption is the main pathway by which activated carbon material function. The advantages of this mechanism include rate and capacity effectiveness, however, the adsorption can be reversed at changes in temperature or humidity. Catalysis involves the conversion of an odor compound to another compound. Ideally, the converted compound should be heavier and posses a higher boiling point and/or a lower vapor pressure, thus not allowing it to be re-emitted into the atmosphere. This is not guaranteed or predictable, however, and may lead to disadvantages compared to something that is more irreversible. Chemical absorption involves the chemical binding of the odor compound to the odor removal compound. Typically, the binding is irreversible when subject to physical challenges such as temperature and humidity. It has been shown that odorous compounds are removed from metal-modified silica nano-particles via the catalytic mechanism when the metal-modified silica nano-particles are prepared without the presence of ultrasound energy.

Based on the foregoing, there is a need in the art for a method of preparing metal-modified silica particles by ultrasonically mixing a first and second formulation. Furthermore, it would be advantageous if the system could be configured to enhance the cavitation mechanism of the ultrasonics, thereby decreasing particle agglomeration and changing the mechanism by which odorous compounds will be removed during use of the metal-modified particles.

SUMMARY OF DISCLOSURE

In one aspect, a method for preparing metal-modified particles by ultrasonically mixing a first and second formulation comprises providing a treatment chamber comprising an elongate housing having longitudinally opposite ends and an interior space. The housing is generally closed at a first longitudinal end and generally open at a second longitudinal end for receiving a first and second formulation into the interior space of the housing, and at least one outlet port through which a particulate-containing formulation is exhausted from the housing following ultrasonic mixing of the first and second formulations. The outlet port is spaced longitudinally from the second longitudinal end such that liquid (i.e., first and/or second formulations) flows longitudinally within the interior space of the housing from the second longitudinal end to the outlet port. In one embodiment, the housing includes more than two separate ports for receiving additional formulations to be mixed to prepare the metal-modified particles. At least one elongate ultrasonic waveguide assembly extends longitudinally within the interior space of the housing and is operable at a predetermined ultrasonic frequency to ultrasonically energize and mix the first and second formulations (and any additional formulations) flowing within the housing.

The waveguide assembly generally comprises an elongate ultrasonic horn disposed at least in part intermediate the second longitudinal end and the outlet port of the housing and has an outer surface located for contact with the first and second formulations flowing within the housing from the second longitudinal end to the outlet port. A plurality of discrete agitating members are in contact with and extend transversely outward from the outer surface of the horn intermediate the second longitudinal end and the outlet port in longitudinally spaced relationship with each other. The agitating members and the horn are constructed and arranged for dynamic motion of the agitating members relative to the horn upon ultrasonic vibration of the horn at the predetermined frequency and to operate in an ultrasonic cavitation mode of the agitating members corresponding to the predetermined frequency and the first and second formulations being mixed within the chamber.

As such, the present disclosure is directed to a method for preparing metal-modified particles. The method comprises providing a treatment chamber comprising an elongate housing having longitudinally opposite ends and an interior space, and an elongate ultrasonic waveguide assembly extending longitudinally within the interior space of the housing and being operable at a predetermined ultrasonic frequency to ultrasonically energize and mix a first and a second formulation flowing within the housing to prepare the metal-modified particles. The housing is closed at a first longitudinal end and open at a second longitudinal end for receiving a first and second formulation into the interior space of the housing, and at least one outlet port through which a particulate-containing formulation is exhausted from the housing following ultrasonic mixing of the first and second formulations. The outlet port is spaced longitudinally from the second longitudinal end such that the first and second formulations flow longitudinally within the interior space of the housing from the second longitudinal end to the outlet port.

The waveguide assembly comprises an elongate ultrasonic horn disposed at least in part intermediate the second longitudinal end and the outlet port of the housing and having an outer surface located for contact with the first and second formulations flowing within the housing from the second longitudinal end to the outlet port. Additionally, the waveguide assembly comprises a plurality of discrete agitating members in contact with and extending transversely outward from the outer surface of the horn intermediate the second longitudinal end and the outlet port in longitudinally spaced relationship with each other. The agitating members and the horn are constructed and arranged for dynamic motion of the agitating members relative to the horn upon ultrasonic vibration of the horn at the predetermined frequency and to operate in an ultrasonic cavitation mode of the agitating members corresponding to the predetermined frequency and the first and second formulations being mixed in the chamber.

The method further includes delivering the second formulation via the first inlet port into the interior space of the housing, delivering the second formulation via the second inlet port into the interior space of the housing, and ultrasonically mixing the first and second formulations via the elongate ultrasonic waveguide assembly operating in the predetermined ultrasonic frequency.

The present invention is further directed to a method for preparing metal-modified particles. The method comprises providing a treatment chamber comprising an elongate housing having longitudinally opposite ends and an interior space, and an elongate ultrasonic waveguide assembly extending longitudinally within the interior space of the housing and being operable at a predetermined ultrasonic frequency to ultrasonically energize and mix a first and second formulation flowing within the housing. The housing is generally closed at at least one of its longitudinal ends and has at least a first inlet port for receiving the first formulation into the interior space of the housing, and a second inlet port for receiving the second formulation into the interior space of the housing, and at least one outlet port through which a particulate-containing formulation is exhausted from the housing following ultrasonic mixing of the first and second formulations. The outlet port is spaced longitudinally from the first and second inlet ports such that the first and second formulations flow longitudinally within the interior space of the housing from the first and second inlet ports to the outlet port.

The waveguide assembly comprises an elongate ultrasonic horn disposed at least in part intermediate the first and second inlet ports and the outlet port of the housing and having an outer surface located for contact with the first and second formulations flowing within the housing from the first and second inlet ports to the outlet port; a plurality of discrete agitating members in contact with and extending transversely outward from the outer surface of the horn intermediate the first and second inlet ports and the outlet port in longitudinally spaced relationship with each other; and a baffle assembly disposed within the interior space of the housing and extending at least in part transversely inward from the housing toward the horn to direct longitudinally flowing first and second formulations in the housing to flow transversely inward into contact with the agitating members. The agitating members and the horn are constructed and arranged for dynamic motion of the agitating members relative to the horn upon ultrasonic vibration of the horn at the predetermined frequency and to operate in an ultrasonic cavitation mode of the agitating members corresponding to the predetermined frequency and the first and second formulations being mixed in the chamber.

The method further comprises delivering the first formulation via the first inlet port into the interior space of the housing, delivering the second formulation via the second inlet port into the interior space of the housing, and ultrasonically mixing the first and second formulations via the elongate ultrasonic waveguide assembly operating in the predetermined ultrasonic frequency.

The present disclosure is further directed to a method for reducing odor using an ultrasonic mixing system as is described above. The method comprises preparing metal-modified silica particles, isolating the metal-modified silica particles, and contacting the metal modified silica particles to an odorous compound.

Other features of the present disclosure will be in part apparent and in part pointed out hereinafter.

BRIEF DESCRIPTION OF THE DRAWINGS

FIG. 1 is a schematic of an ultrasonic mixing system according to a first embodiment of the present disclosure for preparing metal-modified silica particles.

FIG. 2 is a schematic of an ultrasonic mixing system according to a second embodiment of the present disclosure for preparing metal-modified silica particles.

FIG. 3 is a schematic of an ultrasonic mixing system according to a third embodiment of the present disclosure for preparing metal-modified silica particles.

FIG. 4 depicts a graph showing ethyl mercaptan removal over time as described in Example 1.

FIG. 5 depicts a graph showing remediation of ethyl mercaptan over time as described in Example 5.

FIG. 6 depicts a graph showing headspace gas chromatograms for the remediation of ethyl mercaptan (EtSH).

FIG. 7A depicts mass spectroscopy (MS) chromatograms from GC/MS experiments for the GC peak at approximately 3.5 minutes (r.t.).

FIG. 7B depicts mass spectroscopy (MS) chromatograms from GC/MS experiments for the GC peak at approximately 13.5 minutes (r.t.).

FIG. 8A depicts EPR spectra for copper modified silica particles from Example 2.

FIG. 8B depicts EPR spectra for copper modified silica particles from Example 3.

FIG. 9A depicts XPS spectra for copper modified silica particles from Example 2.

FIG. 9B depicts XPS spectra for copper modified silica particles from Example 3.

Figure 10:
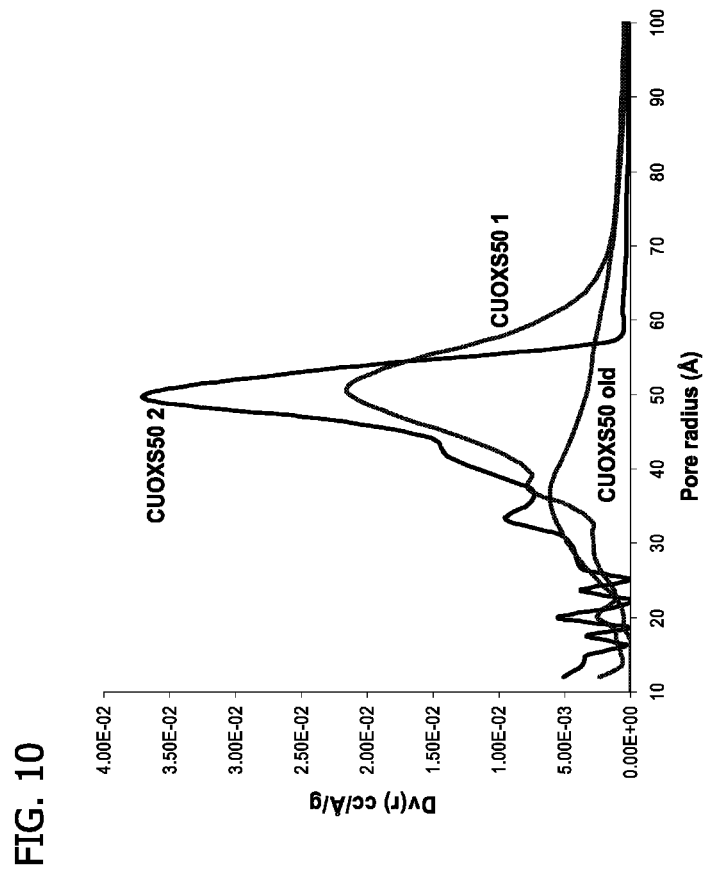

FIG. 10 depicts BJH pore size analyses for copper modified silica particles.

Corresponding reference characters indicate corresponding parts throughout the drawings.

DETAILED DESCRIPTION

With particular reference now to FIG. 1, in one embodiment, an ultrasonic mixing system, generally indicated at 121, for mixing a first and second formulation to prepare metal-modified particles generally comprises a treatment chamber, indicated at 151, that is operable to ultrasonically mix various formulations to form metal-modified particles, and further is capable of creating a cavitation mode that allows for better mixing within the housing of the chamber 151. By ultrasonically mixing the first and second formulations, agglomeration of the silica nano-particles can be significantly reduced, and the mechanism by which metal-modified silica particles remove odorous compounds is changed.

More specifically, by exposing the first and second formulations to ultrasonic energy, a number of factors take advantage of the unique sonochemistry and cavitation activities occurring within the mixture during passage through the chamber that is being mixed by the baffles. While the elemental composition of the metal-modified silica particles is the same as a solution deposition system, it differs in numerous physical and performance characteristics. First, with regard to physical characteristics, the metal is not merely deposited on the surface of the silica particle but rather is imbedded below the subsurface of the particle. Analytically, no trace of the metal can be detected on the surface. Further, the surface area of the particles is higher than that of a solution deposition method system. This is due to small pothole-like holes etched into the surface of the silica particles. In addition, with regard to performance characteristics, the metal species does not have catalytic functionality, but rather, has straight absorption of malodor compounds. Thus, this composition absorbs thiol (mercaptan) odor molecules and locks them into a complex. Although this composition does eventually reach a saturation point, which is in contrast to the solution deposition composition, these metal-modified particles are still a very effective odor/malodor absorbent. As such, it can be concluded that a different type of metal complex species has been generated using method of preparation inclusive of the presence of ultrasonic energy.

While not fully understood, it is believed that in the ultrasonic chamber, the metal ions are forcefully imbedded into the sub-surface of the nano-particles by the extraordinary forces involved in the cavitation process. The localized high temperatures and pressures may also contribute to the new metal complex formed therein.

It is generally believed that as ultrasonic energy is created by the waveguide assembly, increased cavitation of the formulations occurs, creating microbubbles. As these microbubbles then collapse, the pressure within the chamber is increased forcibly dispersing the particles of the second formulation within and throughout the first and second formulations.

More specifically, ultrasonic cavitation is a process by which extreme pressures, temperatures, and velocities can be generated on a very small scale for very short periods of time. The mechanism producing these conditions is the nucleation, growth, and violent collapse of cavitation "bubbles". These bubbles are formed in several ways when mechanical pressure waves (alternating compression and rarefaction) are introduced into a fluid. During the rarefaction phase of the pressure wave, the liquid molecules are pulled against the liquid's natural elastic and molecular bonding forces. With sufficient intensity, the negative pressure can exceed the tensile strength of the liquid and generate a vacuum nucleus in the liquid. The voids typically form first at natural "weak" points in the liquid such as entrained gas in the pores of suspended particulates or small remnant bubbles from previous cavitation events, however, these are not a requirement. During the compression phase of the wave, the void collapses.

Once a bubble is formed, if the expansion phase is fast enough, the bubble will not be able to fully collapse and it will continue to grow until it reaches a size described as the resonant point (in water, 170 microns at 20 kHz). At this size, the bubble can efficiently absorb the ultrasound energy, and the bubble grows rapidly until it reaches a size where the efficient absorption diminishes and the bubble violently collapses.

Another means by which bubble growth occurs at a slower pace is described as "rectified diffusion". A small gas bubble grows during the rarefaction phase of the mechanical pressure wave and gas begins to diffuse into the bubble from the liquid. As the bubble begins to shrink during the compression phase of the mechanical pressure wave, gas begins to diffuse out of the bubble back into the liquid. The rate of diffusion is directly related to the surface area of the bubble. On average, the bubble surface area is smaller during the compression phase than it is during the expansion phase. Therefore, more gas diffuses into the bubble than can diffuse out so the oscillating bubble grows. Once a critical size is reached, the process can no longer sustain itself and the bubble collapses.

In either situation, the violent collapse results in the rapid (much less than a microsecond) compression of the gas to a pressure of about 1,000 atmospheres resulting in a temperature increase of about 5000° C. The shock waves produced by the numerous cavitation events result in extremely turbulent micro-mixing and high-speed particle collisions. These inter-particle collisions have been shown to be sufficiently energetic to melt together metal particles at transient temperatures determined to be up to about 3000° C. at the point of collision. The inter-particle collisions can also have a dramatic effect on particle morphology remarkably changing the size, surface, and composition of particles.

When a cavitation bubble is formed and collapses near a surface, another phenomenon is observed. Due to the non-homogeneous boundary conditions, the bubble implodes asymmetrically and generates a very small, high-velocity (measured at about 400 km/hr) jet of liquid toward the surface. This energetic jet can cause severe damage to surfaces and is the effect responsible for the cavitation erosion that is observed during ultrasonic liquid processing, as well as any high-speed fluid flow event that results in cavitation (e.g., liquid pumping, ship propellers).

When a cavitation bubble is formed and collapses away from a surface, it does so symmetrically (spherically). A surface must be several times larger than the bubble to generate asymmetrical bubble collapse. Therefore, fine particle dispersions will not produce the liquid jetting effect.

The ultrasonic cavitation effect is influenced by the frequency and intensity of the mechanical pressure waves generated within the liquid as well as the properties of the liquid itself. The number of cavitation sites is known to be directly proportional to the excitation frequency, however, the average size of the cavitation bubble is inversely proportional to the frequency. In water at 20 kHz, the cavitation threshold intensity has been empirically determined to be 0.3 W/cm$^2$. Liquid properties that influence cavitation include vapor pressure, temperature, density, viscosity, and surface tension.

The ultrasonic treatment device described herein has an advantage over most other known devices in that it can achieve acoustic intensities several (3 or more) orders of magnitude above the cavitation threshold level and significantly higher than other commercial systems.

The terms "liquid" and "formulation" are used interchangeably to refer to a single component formulation, a formulation comprised of two or more components in which at least one of the components is a liquid such as a liquid-liquid formulation, a liquid-gas formulation, or a liquid-solid formulation.

The ultrasonic mixing system 121 is illustrated schematically in FIG. 1 and further described herein with reference to use of the treatment chamber 151 in the ultrasonic mixing system to mix various formulations to create metal-modified particles. The metal-modified particles can subsequently be used to remove odorous compounds from a medium such as air or water. For example, in one embodiment, a first formulation comprising aqueous sodium bicarbonate is ultrasonically mixed with a second formulation comprising silica nano-particles and a copper (II) salt aqueous formulation to form copper-modified silica nano-particles for use in removing odorous compounds. It should be understood by one skilled in the art that while described herein with respect to a first formulation comprising aqueous sodium bicarbonate and a second formulation comprising silica nano-particles and a chloride salt of copper(II) aqueous formulation, the first formulation may comprise any basic buffer system and the second formulation may comprise silica nano-particles with a chloride salt of any transition metal.

Specifically, the first formulation may comprise any basic buffer system capable of maintaining the pH of the first formulation from about 8 to about 10. For instance, the basic buffer system may include potassium hydroxide, sodium hydroxide, ammonium hydroxide, sodium carbonate, and combinations thereof. Without intending to be limited by theory, it is believed that the purpose of the base in the buffer system is to deprotonate the silanol groups on the silica surface, which allows the transition metal to chemically form a bond with the deprotonated silanol.

Further, the silica nano-particles included within the second formulation may possess various forms, shapes, and sizes depending upon the desired result. For instance, the silica particles may be in the shape of a sphere, crystal, rod, disk, tube, string, and the like. The average size of the silica particles is generally less than about 500 microns, in some embodiments less than about 100 microns, in some embodiments less than about 100 nanometers, in some embodiments from about 1 to about 50 nanometers, in some embodiments from about 2 to about 50 nanometers, and in some embodiments, from about 4 to about 20 nanometers. As used herein, the average size of a particle refers to its average length, width, height, and/or diameter.

The silica particles may have a surface area of from about 50 square meters per gram ($m^2/g$) to about 1000 $m^2/g$, in some embodiments from about 100 $m^2/g$ to about 600 $m^2/g$, and in some embodiments, from about 180 $m^2/g$ to about 240 $m^2/g$. Surface area may be determined by the physical gas adsorption (B.E.T.) method of Brunauer, Emmet, and Teller, Journal of American Chemical Society, Vol. 60, 1938, p. 309, with nitrogen as the adsorption gas. If desired, the silica particles may also be relatively nonporous or solid. That is, the silica particles may have a pore volume that is less than about 0.5 milliliters per gram (ml/g), in some embodiments less than about 0.4 milliliters per gram, in some embodiments less than about 0.3 ml/g, and in some embodiments, from about 0.2 ml/g to about 0.3 ml/g. Without intending to be limited by theory, it is believed that silica particles having such small size and high surface area may improve the adsorption capability of the silica for many odorous compounds. Moreover, it is believed that the solid nature, i.e., low pore volume, of the silica particles may enhance the uniformity and stability of the silica, without sacrificing its odor adsorption characteristics. Commercially available examples of silica nano-particles, such as described above, include SNOWTEX-C®, SNOWTEX-O®, SNOWTEX-PS®, and SNOWTEX-OXS®, which are available from Nissan Chemical America Corporation of Houston, Tex. SNOWTEX-OXS® particles, for instance, have a particle size of from 4 to 6 nanometers, and may be ground into a powder having a surface area of approximately 509 square meters per gram.

The concentration of silica particles in the second formulation is from about 0.01% to about 10% (by weight) in water. In one embodiment, the concentration of silica particles in the second formulation is at least about 4% (by weight) in water. In another embodiment, the concentration of silica particles in the second formulation is about 5% (by weight) in water.

Although described herein with respect to silica, other materials may be used in accordance with the present disclosure to form metal modified particles. For instance, the particles could be selected from inorganic materials, such as silica, alumina, or zeolite; metals, such as silver, copper, or gold; organic materials, such as polystyrene, latex, polyethylene glycol, or a lipid micelle; or a microbe including a lipid or saccharide-based wall. Further, the present disclosure may be used in preparing metal-modified flat surfaces comprised of metal, organic films, inorganic films, sheets, or fibers.

In addition, the second formulation may comprise silica nano-particles with a salt of any transition metal. Examples of suitable transition metals that may be used in the methods of the present disclosure, include, but are not limited to, scandium, titanium, vanadium, chromium, manganese, iron, cobalt, nickel, copper, zinc, silver, and gold. The second formulation may comprise silica nano-particles with chloride salts of Cu(II), Fe(II), Mn(II), and Co(II). Without being limited by theory, it is believed that the transition metal provides one or more active sites for capturing and/or neutralizing an odorous compound. Further, the presence of the transition metal is also believed to help improve the Lewis acidity of the silica, thus rendering it more receptive to free electron pairs of many odorous compounds. In addition, the point of contact for chemical absorption of the odor compound to the metal-modified silica particle is the metal site. In an alternative embodiment, other materials may also be used in the second formulation in accordance with the present disclosure. These other materials may include metals; organic molecules, such as dyes, pharmaceuticals, antimicrobials, UV absorbing molecules, and the like; enzymes, biomolecules; and microbes, such as bacteria, molds, viruses, and spores. These embedded species may be used for ease of handling, use, and removal, and could also be used as triggerable controlled release systems which could release these embedded species when needed.

The transition metal is present in the second formulation from about 13% to about 40% by weight of the second formulation. The ratio of the transition metal to the silica particles present in the second formulation may be selectively varied to achieve the desired results. In most embodiments, for example, the ratio of the transition metal to the silica particles is at least about 5:1, in some embodiments at least about 50:1, and in some embodiments, at least about 200:1. In a preferred embodiment, the second formulation comprises silica particles dispersed in a chloride salt of copper(II) aqueous formulation in a ratio of about 50:1.

In one particularly preferred embodiment, as illustrated in FIG. 1, the treatment chamber 151 is generally elongate and has a general inlet end 125 (an upper end in the orientation of the illustrated embodiment) and a general outlet end 127 (a lower end in the orientation of the illustrated embodiment). The treatment chamber 151 is configured such that the first formulation enters the treatment chamber 151 generally at the inlet end 125 thereof, flows generally longitudinally within the chamber (e.g., downward in the orientation of illustrated embodiment) and exits the chamber generally at the outlet end 127 of the chamber.

The terms "upper" and "lower" are used herein in accordance with the vertical orientation of the treatment chamber 151 illustrated in the various drawings and are not intended to describe a necessary orientation of the chamber in use. That is, while the chamber 151 is most suitably oriented vertically, with the outlet end 127 of the chamber below the inlet end 125 as illustrated in the drawing, it should be understood that the chamber may be oriented with the inlet end below the outlet end and the first and second formulations are mixed as the first formulation travels upward through the chamber, or it may be oriented other than in a vertical orientation and remain within the scope of this disclosure.

The terms "axial" and "longitudinal" refer directionally herein to the vertical direction of the chamber 151 (e.g., end-to-end such as the vertical direction in the illustrated embodiment of FIG. 1). The terms "transverse", "lateral" and "radial" refer herein to a direction normal to the axial (e.g., longitudinal) direction. The terms "inner" and "outer" are also used in reference to a direction transverse to the axial direction of the treatment chamber 151, with the term "inner" referring to a direction toward the interior of the chamber and the term "outer" referring to a direction toward the exterior of the chamber.

The inlet end 125 of the treatment chamber 151 is in fluid communication with a suitable delivery system, generally indicated at 129, that is operable to direct one formulation to, and more suitably through, the chamber 151. Typically, the delivery system 129 may comprise one or more pumps 171 operable to pump the respective formulation from a corresponding source thereof to the inlet end 125 of the chamber 151 via suitable conduits 134.

It is understood that the delivery system 129 may be configured to deliver more than one formulation to the treatment chamber 151 without departing from the scope of this disclosure. It is also contemplated that delivery systems other than that illustrated in FIG. 1 and described herein may be used to deliver one or more formulations to the inlet end 125 of the treatment chamber 151 without departing from the scope of this disclosure. It should be understood that more than one formulation can refer to two streams of the same formulation or different formulations being delivered to the inlet end of the treatment chamber without departing from the scope of the present disclosure.

The treatment chamber 151 comprises a housing defining an interior space 153 of the chamber 151 through which the first formulation delivered to the chamber 151 flows from the inlet end 125 to the outlet end 127 thereof after the second formulation has been added to the chamber 151. The chamber housing 151 suitably comprises an elongate tube 155 generally defining, at least in part, a sidewall 157 of the chamber 151. It should be understood by one skilled in the art that the inlet end of the housing may include one or more inlet ports, two or more inlet ports, and even three or more inlet ports. For example, FIG. 3, as discussed in more detail below, illustrates an embodiment comprising an inlet port for delivering the first formulation to the chamber and a separate inlet port for delivering the second formulation to the chamber. Alternatively, although not shown, the housing may comprise three inlet ports, wherein the first inlet port and the second inlet port are suitable in parallel, spaced relationship with each other, and the third inlet port is oriented on the opposite sidewall of the housing from the first and second inlet ports. Further, it should be understood by one skilled in the art that an open longitudinal end of the elongate tube 155 may be used as an inlet or an outlet port.

As shown in FIG. 1, the inlet end 125 is generally open to the surrounding environment. In an alternative embodiment (not shown), however, the housing may comprise a closure connected to and substantially closing the longitudinally opposite end of the sidewall, and having at least one inlet port therein to generally define the inlet end of the treatment chamber. The sidewall (e.g., defined by the elongate tube) of the chamber has an inner surface that together with the waveguide assembly (as described below) and the closure define the interior space of the chamber.

In the illustrated embodiment of FIG. 1, the tube 155 is generally cylindrical so that the chamber sidewall 157 is generally annular in cross-section. However, it is contemplated that the cross-section of the chamber sidewall 157 may be other than annular, such as polygonal or another suitable shape, and remains within the scope of this disclosure. The chamber sidewall 157 of the illustrated chamber 151 is suitably constructed of a transparent material, although it is understood that any suitable material may be used as long as the material is compatible with the formulations and particulates being mixed within the chamber, the pressure at which the chamber is intended to operate, and other environmental conditions within the chamber such as temperature.

A waveguide assembly, generally indicated at 203, extends longitudinally at least in part within the interior space 153 of the chamber 151 to ultrasonically energize the formulation (and any of its components) flowing through the interior space 153 of the chamber 151. In particular, the waveguide assembly 203 of the illustrated embodiment extends longitudinally from the lower or outlet end 127 of the chamber 151 up into the interior space 153 thereof to a terminal end 113 of the waveguide assembly disposed intermediate the inlet end 125. Although illustrated in FIG. 1 as extending longitudinally into the interior space 153 of the chamber 151, it should be understood by one skilled in the art that the waveguide assembly may extend laterally from a housing sidewall of the chamber, running horizontally through the interior space thereof without departing from the scope of the present disclosure. Typically, the waveguide assembly 203 is mounted, either directly or indirectly, to the chamber housing 151 as will be described later herein.

Still referring to FIG. 1, the waveguide assembly 203 suitably comprises an elongate horn assembly, generally indicated at 133, disposed entirely with the interior space 153 of the housing 151 intermediate the inlet end 125 and the outlet port 165 for complete submersion within the liquid being treated within the chamber 151, and more suitably, in the illustrated embodiment, it is aligned coaxially with the chamber sidewall 157. The horn assembly 133 has an outer surface 107 that together with an inner surface 167 of the sidewall 157 defines a flow path within the interior space 153 of the chamber 151 along which the formulation (and its components) flow past the horn within the chamber (this portion of the flow path being broadly referred to herein as the ultrasonic treatment zone). The horn assembly 133 has an upper end defining a terminal end of the horn assembly (and therefore the terminal end 113 of the waveguide assembly) and a longitudinally opposite lower end 111. Although not shown, it is particularly preferable that the waveguide assembly 203 also comprises a booster coaxially aligned with and connected at an upper end thereof to the lower end 111 of the horn assembly 133. It is understood, however, that the waveguide assembly 203 may comprise only the horn assembly 133 and remain within the scope of this disclosure. It is also contemplated that the booster may be disposed entirely exterior of the chamber housing 151, with the horn assembly 133 mounted on the chamber housing 151 without departing from the scope of this disclosure.

The waveguide assembly 203, and more particularly the booster is suitably mounted on the chamber housing 151, e.g., on the tube 155 defining the chamber sidewall 157, at the upper end thereof by a mounting member (not shown) that is configured to vibrationally isolate the waveguide assembly (which vibrates ultrasonically during operation thereof) from the treatment chamber housing. That is, the mounting member inhibits the transfer of longitudinal and transverse mechanical vibration of the waveguide assembly 203 to the chamber housing 151 while maintaining the desired transverse position of the waveguide assembly (and in particular the horn assembly 133) within the interior space 153 of the chamber housing and allowing both longitudinal and transverse displacement of the horn assembly within the chamber housing. The mounting member also at least in part (e.g., along with the booster, lower end of the horn assembly) closes the outlet end 127 of the chamber 151. Examples of suitable mounting member configurations are illustrated and described in U.S. Pat. No. 6,676,003, the entire disclosure of which is incorporated herein by reference to the extent it is consistent herewith.

In one particularly suitable embodiment, the mounting member is of single piece construction. Even more suitably the mounting member may be formed integrally with the booster (and more broadly with the waveguide assembly 203). However, it is understood that the mounting member may be constructed separately from the waveguide assembly 203 and remain within the scope of this disclosure. It is also understood that one or more components of the mounting member may be separately constructed and suitably connected or otherwise assembled together.

In one suitable embodiment, the mounting member is further constructed to be generally rigid (e.g., resistant to static displacement under load) so as to hold the waveguide assembly 203 in proper alignment within the interior space 153 of the chamber 151. For example, the rigid mounting member in one embodiment may be constructed of a non-elastomeric material, more suitably metal, and even more suitably the same metal from which the booster (and more broadly the waveguide assembly 203) is constructed. The term "rigid" is not, however, intended to mean that the mounting member is incapable of dynamic flexing and/or bending in response to ultrasonic vibration of the waveguide assembly 203. In other embodiments, the rigid mounting member may be constructed of an elastomeric material that is sufficiently resistant to static displacement under load but is otherwise capable of dynamic flexing and/or bending in response to ultrasonic vibration of the waveguide assembly 203.

A suitable ultrasonic drive system 131 including at least an exciter (not shown) and a power source (not shown) is disposed exterior of the chamber 151 and operatively connected to the booster (not shown) (and more broadly to the waveguide assembly 203) to energize the waveguide assembly to mechanically vibrate ultrasonically. Examples of suitable ultrasonic drive systems 131 include a Model 20A3000 system available from Dukane Ultrasonics of St. Charles, Ill., and a Model 2000CS system available from Herrmann Ultrasonics of Schaumberg, Ill.

In one embodiment, the drive system 131 is capable of operating the waveguide assembly 203 at a frequency in the range of about 15 kHz to about 100 kHz, more suitably in the range of about 15 kHz to about 60 kHz, and even more suitably in the range of about 20 kHz to about 40 kHz. Such ultrasonic drive systems 131 are well known to those skilled in the art and need not be further described herein.

In some embodiments, however not illustrated, the treatment chamber can include more than one waveguide assembly having at least two horn assemblies for ultrasonically treating and mixing the phases together to prepare the emulsion. As noted above, the treatment chamber comprises a housing defining an interior space of the chamber through which the formulations are delivered from an inlet end. The housing comprises an elongate tube defining, at least in part, a sidewall of the chamber. As with the embodiment including only one waveguide assembly as described above, the tube may have one or more inlet ports formed therein, through which at least two formulations to be mixed within the chamber are delivered to the interior space thereof, and at least one outlet port through which the particulate-containing formulation exits the chamber.

In such an embodiment, two or more waveguide assemblies extend longitudinally at least in part within the interior space of the chamber to ultrasonically energize and mix the formulations (and resulting particulate containing formulation) flowing through the interior space of the chamber. Each waveguide assembly separately includes an elongate horn assembly, each disposed entirely within the interior space of the housing intermediate the inlet end 125 and the outlet port for complete submersion within the formulations being mixed within the chamber. Each horn assembly can be independently constructed as described more fully herein (including the horns, along with the plurality of agitating members and baffle assemblies).

Referring back to FIG. 1, the horn assembly 133 comprises an elongate, generally cylindrical horn 105 having an outer surface 107, and two or more (i.e., a plurality of) agitating members 137 connected to the horn and extending at least in part transversely outward from the outer surface of the horn in longitudinally spaced relationship with each other. The horn 105 is suitably sized to have a length equal to about one-half of the resonating wavelength (otherwise commonly referred to as one-half wavelength) of the horn. In one particular embodiment, the horn 105 is suitably configured to resonate in the ultrasonic frequency ranges recited previously, and most suitably at 20 kHz. For example, the horn 105 may be suitably constructed of a titanium alloy (e.g., $Ti_6Al_4V$) and sized to resonate at 20 kHz. The one-half wavelength horn 105 operating at such frequencies thus has a length (corresponding to a one-half wavelength) in the range of about 4 inches to about 6 inches, more suitably in the range of about 4.5 inches to about 5.5 inches, even more suitably in the range of about 5.0 inches to about 5.5 inches, and most suitably a length of about 5.25 inches (133.4 mm). It is understood, however, that the treatment chamber 151 may include a horn 105 sized to have any increment of one-half wavelength without departing from the scope of this disclosure.

In one embodiment (not shown), the agitating members 137 comprise a series of five washer-shaped rings that extend continuously about the circumference of the horn in longitudinally spaced relationship with each other and transversely outward from the outer surface of the horn. In this manner the vibrational displacement of each of the agitating members relative to the horn is relatively uniform about the circumference of the horn. It is understood, however, that the agitating members need not each be continuous about the circumference of the horn. For example, the agitating members may instead be in the form of spokes, blades, fins or other discrete structural members that extend transversely outward from the outer surface of the horn. For example, as illustrated in FIG. 1, one of the five agitating members is in a T-shape 701. Specifically, the T-shaped agitating member 701 surrounds the nodal region. It has been found that members in the T-shape, generate a strong radial (e.g., horizontal) acoustic wave that further increases the cavitation effect as described more fully herein.

By way of a dimensional example, the horn assembly 133 of the illustrated embodiment of FIG. 1 has a length of about 5.25 inches (133.4 mm), one of the rings 137 is suitably disposed adjacent the terminal end 113 of the horn 105 (and hence of the waveguide assembly 203), and more suitably is longitudinally spaced approximately 0.063 inches (1.6 mm) from the terminal end of the horn 105. In other embodiments the uppermost ring may be disposed at the terminal end of the horn 105 and remain within the scope of this disclosure. The rings 137 are each about 0.125 inches (3.2 mm) in thickness and are longitudinally spaced from each other (between facing surfaces of the rings) a distance of about 0.875 inches (22.2 mm).

It is understood that the number of agitating members 137 (e.g., the rings in the illustrated embodiment) may be less than or more than five without departing from the scope of this disclosure. It is also understood that the longitudinal spacing between the agitating members 137 may be other than as illustrated in FIG. 1 and described above (e.g., either closer or spaced further apart). Furthermore, while the rings 137 illustrated in FIG. 1 are equally longitudinally spaced from each other, it is alternatively contemplated that where more than two agitating members are present the spacing between longitudinally consecutive agitating members need not be uniform to remain within the scope of this disclosure.

In particular, the locations of the agitating members 137 are at least in part a function of the intended vibratory displacement of the agitating members upon vibration of the horn assembly 133. For example, in the illustrated embodiment of FIG. 1, the horn assembly 133 has a nodal region located generally longitudinally centrally of the horn 105 (e.g., at the third ring). As used herein and more particularly shown in FIG. 1, the "nodal region" of the horn 105 refers to a longitudinal region or segment of the horn member along which little (or no) longitudinal displacement occurs during ultrasonic vibration of the horn and transverse (e.g., radial in the illustrated embodiment) displacement of the horn is generally maximized. Transverse displacement of the horn assembly 133 suitably comprises transverse expansion of the horn but may also include transverse movement (e.g., bending) of the horn.

In the illustrated embodiment of FIG. 1, the configuration of the one-half wavelength horn 105 is such that the nodal region is particularly defined by a nodal plane (i.e., a plane transverse to the horn member at which no longitudinal displacement occurs while transverse displacement is generally maximized) is present. This plane is also sometimes referred to as a "nodal point". Accordingly, agitating members 137 (e.g., in the illustrated embodiment, the rings) that are disposed longitudinally further from the nodal region of the horn 105 will experience primarily longitudinal displacement while agitating members that are longitudinally nearer to the nodal region will experience an increased amount of transverse displacement and a decreased amount of longitudinal displacement relative to the longitudinally distal agitating members.

It is understood that the horn 105 may be configured so that the nodal region is other than centrally located longitudinally on the horn member without departing from the scope of this disclosure. It is also understood that one or more of the agitating members 137 may be longitudinally located on the horn so as to experience both longitudinal and transverse displacement relative to the horn upon ultrasonic vibration of the horn 105.

Still referring to FIG. 1, the agitating members 137 are sufficiently constructed (e.g., in material and/or dimension such as thickness and transverse length, which is the distance that the agitating member extends transversely outward from the outer surface 107 of the horn 105) to facilitate dynamic motion, and in particular dynamic flexing/bending of the agitating members in response to the ultrasonic vibration of the horn. In one particularly suitable embodiment, for a given ultrasonic frequency at which the waveguide assembly 203 is to be operated in the treatment chamber (otherwise referred to herein as the predetermined frequency of the waveguide assembly) and a particular liquid to be treated within the chamber 151, the agitating members 137 and horn 105 are suitably constructed and arranged to operate the agitating members in what is referred to herein as an ultrasonic cavitation mode at the predetermined frequency.

As used herein, the ultrasonic cavitation mode of the agitating members refers to the vibrational displacement of the agitating members sufficient to result in cavitation (i.e., the formation, growth, and implosive collapse of bubbles in a liquid) of the formulation being prepared at the predetermined ultrasonic frequency. For example, where the formulations (and particulates) flowing within the chamber comprise aqueous liquid formulations, and the ultrasonic frequency at which the waveguide assembly 203 is to be operated (i.e., the predetermined frequency) is about 20 kHZ, one or more of the agitating members 137 are suitably constructed to provide a vibrational displacement of at least 1.75 mils (i.e., 0.00175 inches, or 0.044 mm) to establish a cavitation mode of the agitating members.

It is understood that the waveguide assembly 203 may be configured differently (e.g., in material, size, etc.) to achieve a desired cavitation mode associated with the particular formulation and/or particulates to be mixed. For example, as the viscosity of the formulation being mixed with the particulates changes, the cavitation mode of the agitating members may need to be changed.

In particularly suitable embodiments, the cavitation mode of the agitating members corresponds to a resonant mode of the agitating members whereby vibrational displacement of the agitating members is amplified relative to the displacement of the horn. However, it is understood that cavitation may occur without the agitating members operating in their resonant mode, or even at a vibrational displacement that is greater than the displacement of the horn, without departing from the scope of this disclosure.

In one suitable embodiment, a ratio of the transverse length of at least one and, more suitably, all of the agitating members to the thickness of the agitating member is in the range of about 2:1 to about 6:1. As another example, the rings each extend transversely outward from the outer surface 107 of the horn 105 a length of about 0.5 inches (12.7 mm) and the thickness of each ring is about 0.125 inches (3.2 mm), so that the ratio of transverse length to thickness of each ring is about 4:1. It is understood, however that the thickness and/or the transverse length of the agitating members may be other than that of the rings as described above without departing from the scope of this disclosure. Also, while the agitating members 137 (rings) may suitably each have the same transverse length and thickness, it is understood that the agitating members may have different thicknesses and/or transverse lengths.

In the above described embodiment, the transverse length of the agitating member also at least in part defines the size (and at least in part the direction) of the flow path along which the formulations and particulates or other flowable components in the interior space of the chamber flows past the horn. For example, the horn may have a radius of about 0.875 inches (22.2 mm) and the transverse length of each ring is, as discussed above, about 0.5 inches (12.7 mm). The radius of the inner surface of the housing sidewall is approximately 1.75 inches (44.5 mm) so that the transverse spacing between each ring and the inner surface of the housing sidewall is about 0.375 inches (9.5 mm). It is contemplated that the spacing between the horn outer surface and the inner surface of the chamber sidewall and/or between the agitating members and the inner surface of the chamber sidewall may be greater or less than described above without departing from the scope of this disclosure.

In general, the horn 105 may be constructed of a metal having suitable acoustical and mechanical properties. Examples of suitable metals for construction of the horn 105 include, without limitation, aluminum, monel, titanium, stainless steel, and some alloy steels. It is also contemplated that all or part of the horn 105 may be coated with another metal such as silver, platinum, gold, palladium, lead dioxide, and copper to mention a few. In one particularly suitable embodiment, the agitating members 137 are constructed of the same material as the horn 105, and are more suitably formed integrally with the horn. In other embodiments, one or more of the agitating members 137 may instead be formed separate from the horn 105 and connected thereto.

While the agitating members 137 (e.g., the rings) illustrated in FIG. 1 are relatively flat, i.e., relatively rectangular in cross-section, it is understood that the rings may have a cross-section that is other than rectangular without departing from the scope of this disclosure. The term "cross-section" is used in this instance to refer to a cross-section taken along one transverse direction (e.g., radially in the illustrated embodiment) relative to the horn outer surface 107). Additionally, as seen of the first two and last two agitating members 137 (e.g., the rings) illustrated in FIG. 1 are constructed only to have a transverse component, it is contemplated that one or more of the agitating members may have at least one longitudinal (e.g., axial) component to take advantage of transverse vibrational displacement of the horn (e.g., at the third agitating member as illustrated in FIG. 1) during ultrasonic vibration of the waveguide assembly 203.

As best illustrated in FIG. 1, the terminal end 113 of the waveguide assembly (e.g., of the horn 105 in the illustrated embodiment) is suitably spaced longitudinally from the inlet end 125 in FIG. 1 to define what is referred to herein as a liquid intake zone in which initial swirling of liquid within the interior space 153 of the chamber housing 151 occurs upstream of the horn 105. This intake zone is particularly useful where the treatment chamber 151 is used for mixing two or more components together (such as with the particulates and the formulation or with two or more components of the formulation from inlet end 125 in FIG. 1) whereby initial mixing is facilitated by the swirling action in the intake zone as the components to be mixed enter the chamber housing 151. It is understood, though, that the terminal end of the horn 105 may be nearer to the inlet end 125 than is illustrated in FIG. 1, and may be substantially adjacent to the inlet end 125 so as to generally omit the intake zone, without departing from the scope of this disclosure.

Additionally, a baffle assembly, generally indicated at 245 is disposed within the interior space 153 of the chamber housing 151, and in particular generally transversely adjacent the inner surface 167 of the sidewall 157 and in generally transversely opposed relationship with the horn 105. In one suitable embodiment, the baffle assembly 245 comprises one or more baffle members 247 disposed adjacent the inner surface 167 of the housing sidewall 157 and extending at least in part transversely inward from the inner surface of the sidewall 167 toward the horn 105. More suitably, the one or more baffle members 247 extend transversely inward from the housing sidewall inner surface 167 to a position longitudinally intersticed with the agitating members 137 that extend outward from the outer surface 107 of the horn 105. The term "longitudinally intersticed" is used herein to mean that a longitudinal line drawn parallel to the longitudinal axis of the horn 105 passes through both the agitating members 137 and the baffle members 247. As one example, in the illustrated embodiment, the baffle assembly 245 comprises four, generally annular baffle members 247 (i.e., extending continuously about the horn 105) longitudinally intersticed with the five agitating members 137.

As a more particular example, the four annular baffle members 247 illustrated in FIG. 1 are of the same thickness as the agitating members 137 in our previous dimensional example (i.e., 0.125 inches (3.2 mm)) and are spaced longitudinally from each other (e.g., between opposed faces of consecutive baffle members) equal to the longitudinal spacing between the rings (i.e., 0.875 inches (22.2 mm)). Each of the annular baffle members 247 has a transverse length (e.g., inward of the inner surface 167 of the housing sidewall 157) of about 0.5 inches (12.7 mm) so that the innermost edges of the baffle members extend transversely inward beyond the outermost edges of the agitating members 137 (e.g., the rings). It is understood, however, that the baffle members 247 need not extend transversely inward beyond the outermost edges of the agitating members 137 of the horn 105 to remain within the scope of this disclosure.

It will be appreciated that the baffle members 247 thus extend into the flow path of the formulations and particulates that flow within the interior space 153 of the chamber 151 past the horn 105 (e.g., within the ultrasonic treatment zone). As such, the baffle members 247 inhibit the formulations and particulates from flowing along the inner surface 167 of the chamber sidewall 157 past the horn 105, and more suitably the baffle members facilitate the flow of the formulations and particulates transversely inward toward the horn for flowing over the agitating members of the horn to thereby facilitate ultrasonic energization (i.e., agitation) of the formulations and particulates to initiate mixing of the formulations and particulates within the carrier liquid to form the metal-modified particles. The baffle members further facilitate the prevention of agglomeration of the particles within the formulations.

In one embodiment, to inhibit gas bubbles against stagnating or otherwise building up along the inner surface 167 of the sidewall 157 and across the face on the underside of each baffle member 247, e.g., as a result of agitation of the phases within the chamber, a series of notches (broadly openings) may be formed in the outer edge of each of the baffle members (not shown) to facilitate the flow of gas (e.g., gas bubbles) between the outer edges of the baffle members and the inner surface of the chamber sidewall. For example, in one particularly preferred embodiment, four such notches are formed in the outer edge of each of the baffle members in equally spaced relationship with each other. It is understood that openings may be formed in the baffle members other than at the outer edges where the baffle members abut the housing, and remain within the scope of this disclosure. It is also understood, that these notches may number more or less than four, as discussed above, and may even be completely omitted.

It is further contemplated that the baffle members 247 need not be annular or otherwise extend continuously about the horn 105. For example, the baffle members 247 may extend discontinuously about the horn 105, such as in the form of spokes, bumps, segments or other discrete structural formations that extend transversely inward from adjacent the inner surface 167 of the housing sidewall 157. The term "continuously" in reference to the baffle members 247 extending continuously about the horn does not exclude a baffle member as being two or more arcuate segments arranged in end-to-end abutting relationship, i.e., as long as no significant gap is formed between such segments. Suitable baffle member configurations are disclosed in U.S. application Ser. No. 11/530, 311 (filed Sep. 8, 2006), which is hereby incorporated by reference to the extent it is consistent herewith.

Also, while the baffle members 247 illustrated in FIG. 1 are each generally flat, e.g., having a generally thin rectangular cross-section, it is contemplated that one or more of the baffle members may each be other than generally flat or rectangular in cross-section to further facilitate the flow of bubbles along the interior space 153 of the chamber 151. The term "cross-section" is used in this instance to refer to a cross-section taken along one transverse direction (e.g., radially in the illustrated embodiment, relative to the horn outer surface 107).

Figure 2:
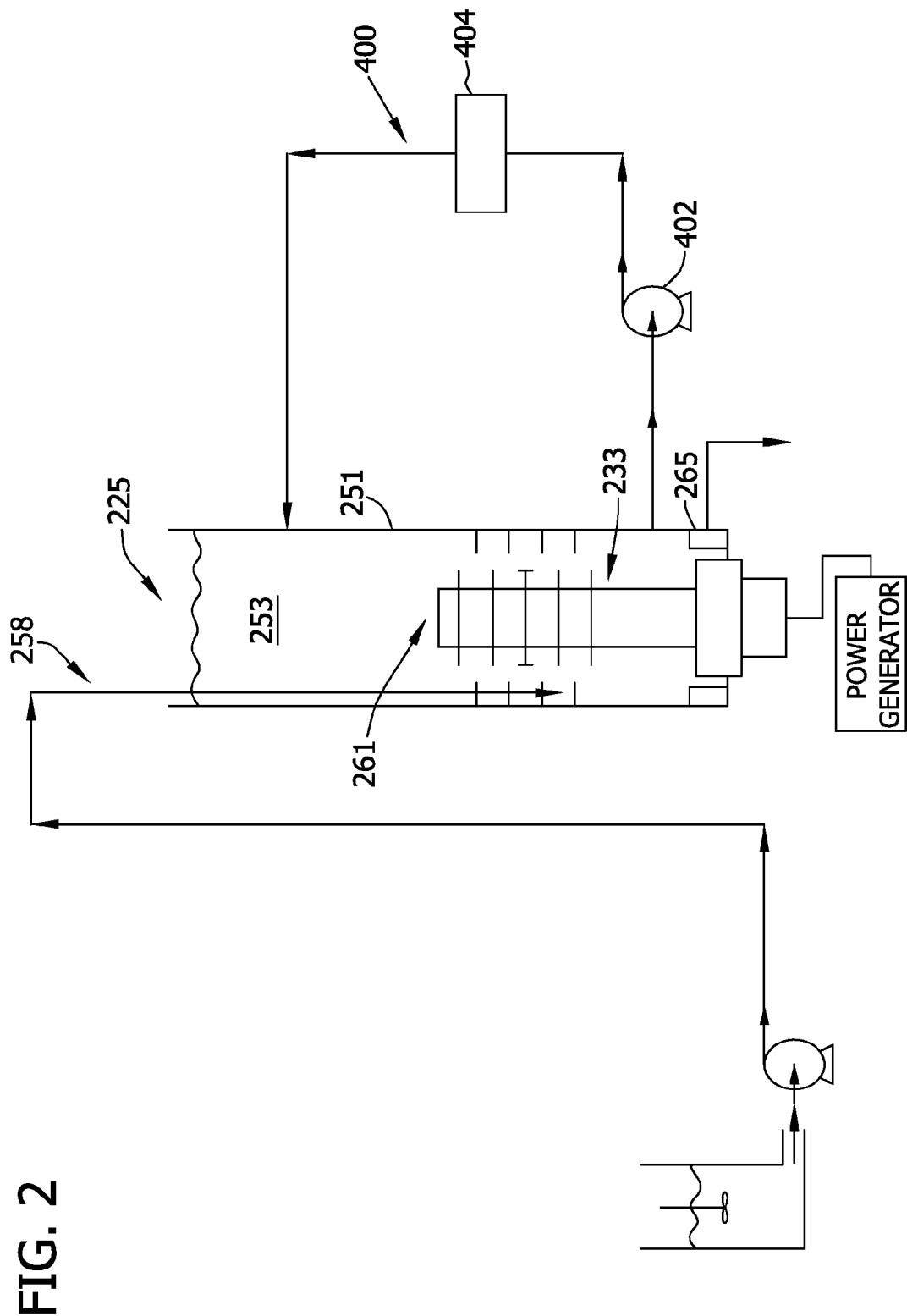

In one embodiment, as illustrated in FIG. 2, the treatment chamber may further be in connection with a liquid recycle loop, generally indicated at 400. Typically, the liquid recycle loop 400 is disposed longitudinally between the inlet end 225 and the outlet port 265. The liquid recycle loop 400 recycles a portion of the first and second formulations being mixed within the interior space 253 of the housing 251 back into the intake zone (generally indicated at 261) of the interior space 253 of the housing 251. By recycling the first and second formulations back into the intake zone, more effective mixing between the formulations (and its components) and particulates can be achieved as the formulations and particulates are allowed to remain within the treatment chamber, undergoing cavitation, for a longer residence time. Furthermore, the agitation in the upper portion of the chamber (i.e., intake zone) can be enhanced, thereby facilitating better dispersing and/or dissolution of the particulates into the formulations.

The liquid recycle loop can be any system that is capable of recycling the liquid formulation from the interior space of the housing downstream of the intake zone back into the intake zone of the interior space of the housing. In one particularly preferred embodiment, as shown in FIG. 2, the liquid recycle loop 400 includes one or more pumps 402 to deliver the formulation back into the intake zone 261 of the interior space 253 of the housing 251. The liquid recycle loop 400 further includes a heat exchanger 404 to cool the formulation passing through the liquid recycle loop 400 prior to re-entering the intake zone 261 of the interior space 253 of the housing 251.

Typically, the first and second formulations (and particulates) are delivered back into the treatment chamber at a flow rate having a ratio of recycle flow rate to initial feed flow rate of the formulations (described below) of 1.0 or greater. While a ratio of recycle flow rate to initial feed flow rate is preferably greater than 1.0, it should be understood that ratios of less than 1.0 can be tolerated without departing from the scope of the present disclosure.

Although the energy created by the ultrasonic horn 233 substantially reduces agglomeration within the treatment chamber, many particulates, when initially added to a formulation, may still attract one another and clump together in large balls. Furthermore, many times, particles in the particulate-containing formulations can settle out over time and attract one another to form large balls; referred to as reagglomeration. As such, in one embodiment, the ultrasonic mixing system may further comprise a filter assembly disposed at the outlet end of the treatment chamber. The filter assembly can filter out the large balls of particulates that form within the particulate-containing formulation prior to the formulation being delivered to a packaging unit for consumer use, as described more fully below. Specifically, the filter assembly is constructed to filter out particulates sized greater than about 0.2 microns.

Specifically, in one particularly preferred embodiment, the filter assembly covers the inner surface of the outlet port. The filter assembly includes a filter having a pore size of from about 0.5 micron to about 20 microns. More suitably, the filter assembly includes a filter having a pore size of from about 1 micron to about 5 microns, and even more suitably, about 2 microns. The number and pour size of filters for use in the filter assembly will typically depend on the particulates and formulation to be mixed within the treatment chamber.

A degasser may also be included in the ultrasonic mixing system. For example, once the prepared particulate-containing formulation exits the treatment chamber, the particulate-containing formulation flows into a degasser in which excess gas bubbles are removed from the particulate-containing formulation prior to the particulate-containing formulation being used into a consumer end-products.

One particularly preferred degasser is a continuous flow gas-liquid cyclone separator, such as commercially available from NATCO (Houston, Tex.). It should be understood by a skilled artisan, however, that any other system that separates gas from an emulsion by centrifugal action can suitably be used without departing from the present disclosure.

In a third embodiment, the treatment chamber 351 has a general inlet end 325 (a lower end in the orientation of the illustrated embodiment) and a general outlet end 327 (an upper end in the orientation of the illustrated embodiment). The treatment chamber 351 is configured such that the first and second formulations enter the treatment chamber 351 generally at the inlet end 325 thereof, flow generally longitudinally within the chamber (e.g., upward in the orientation of illustrated embodiment) and exit the chamber generally at the outlet end 327 of the chamber. It should be recognized by one skilled in the art that the chamber of this particular embodiment may be oriented other than in a vertical orientation and remain within the scope of this disclosure.

Figure 3:
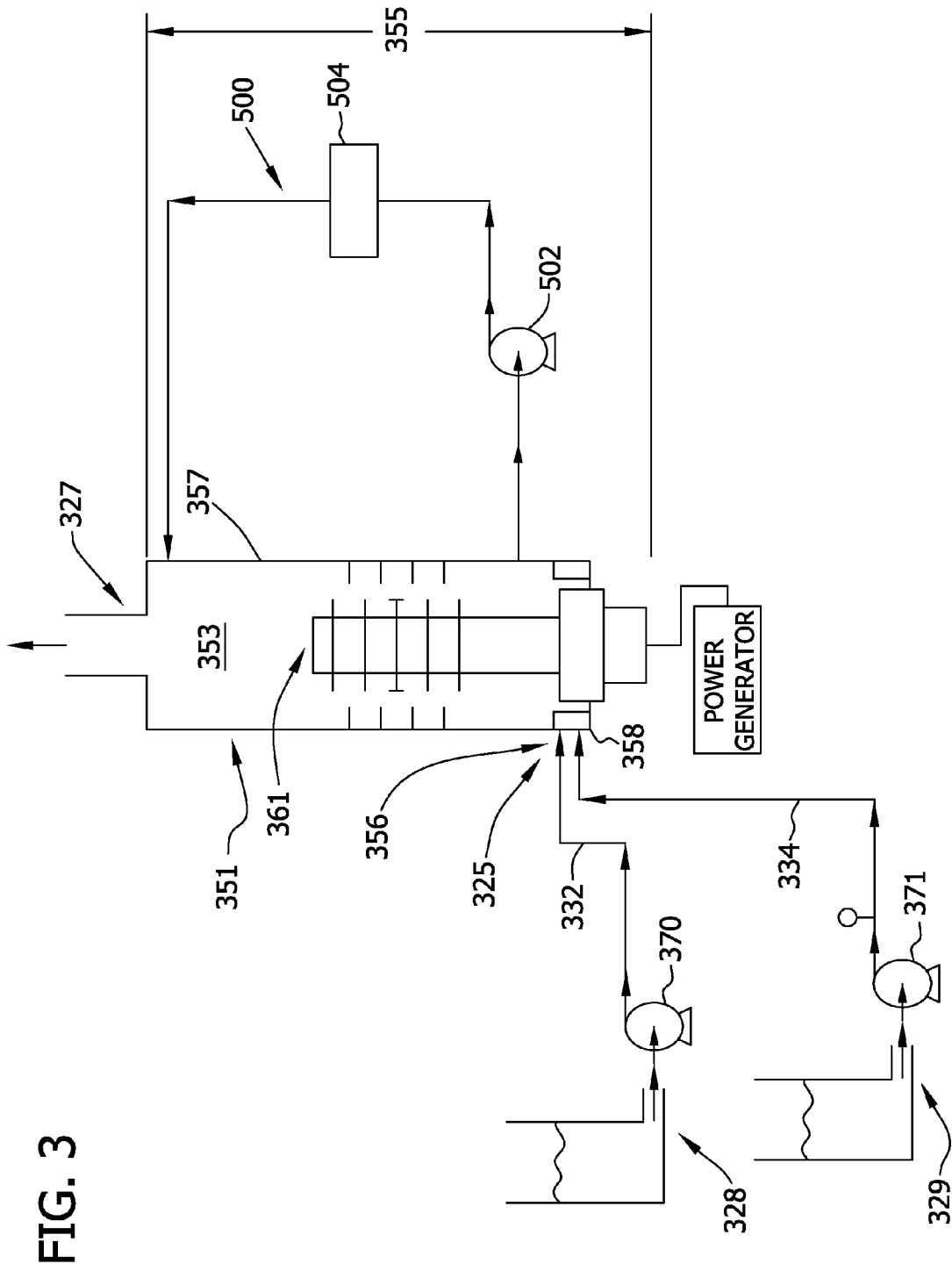

The inlet end 325 of the treatment chamber 351 is typically in fluid communication with at least one suitable delivery system that is operable to direct a formulation to, and more suitably through, the chamber 151. More specifically, as illustrated in FIG. 3, two delivery systems 328 and 329 are operable to direct a first formulation (not shown) and a second formulation (not shown) through the chamber 351. Typically, the delivery systems 328, 329 may independently comprise one or more pumps 370 and 371, respectively, operable to pump the respective phases from corresponding sources thereof to the inlet end 325 of the chamber 351 via suitable conduits 332, 334.

The treatment chamber 351 comprises a housing defining an interior space 353 of the chamber 351 through which at least two formulations delivered to the chamber 351 flow from the inlet end 325 to the outlet end 327 thereof. The chamber housing 351 suitably comprises an elongate tube 355 generally defining, at least in part, a sidewall 357 of the chamber 351. The tube 355 may have one or more inlet ports (two inlet ports are generally indicated in FIG. 3 at 356 and 358) formed therein through which at least two separate formulations to be mixed within the chamber 351 are delivered to the interior space 353 thereof. It should be understood by one skilled in the art that the inlet end of the housing may include more than two inlet ports, more than three ports, and even more than four ports. By way of example, although not shown, the housing may comprise three inlet ports, wherein the first inlet port and the second inlet port are suitably in parallel, spaced relationship with each other, and the third inlet port is oriented on the opposite sidewall of the housing from the first and second inlet ports.

It should also be recognized by one skilled in the art that, while preferably the inlet ports are disposed in close proximity to one another in the inlet end, the inlet ports may be spaced farther along the sidewall of the chamber from one another without departing from the scope of the present disclosure.

As illustrated in FIG. 3, the treatment chamber may further be in connection with a liquid recycle loop, generally indicated at 500. Typically, the liquid recycle loop 500 is disposed longitudinally between the inlet end 325 and the outlet end 327. The liquid recycle loop 500 recycles a portion of the first and second formulations being mixed within the interior space 353 of the housing 351 back into an intake zone (generally indicated at 361) of the interior space 353 of the housing 351. By recycling the first and second formulations back into the intake zone, more effective mixing between the formulations (and its components) and particulates can be achieved as the formulations and particulates are allowed to remain within the treatment chamber, undergoing cavitation, for a longer residence time. Furthermore, the agitation in the upper portion of the chamber (i.e., intake zone) can be enhanced, thereby facilitating better dispersing and/or dissolution of the particulates into the formulations.

The liquid recycle loop can be any system that is capable of recycling the liquid formulation from the interior space of the housing downstream of the intake zone back into the intake zone of the interior space of the housing. In one particularly preferred embodiment, as shown in FIG. 3, the liquid recycle loop 500 includes one or more pumps 502 to deliver the formulation back into the intake zone 361 of the interior space 353 of the housing 351. The liquid recycle loop 500 further includes a heat exchanger 504 to cool the formulation passing through the liquid recycle loop 500 prior to the formulation re-entering the intake zone 361 of the interior space 353 of the housing 351.

Typically, the first and second formulations (and particulates) are delivered back into the treatment chamber at a flow rate having a ratio of recycle flow rate to initial feed flow rate of the formulations (described below) of 1.0 or greater. While a ratio of recycle flow rate to initial feed flow rate is preferably greater than 1.0, it should be understood that ratios of less than 1.0 can be tolerated without departing from the scope of the present disclosure.

In operation according to one embodiment of the ultrasonic mixing system of the present disclosure, the mixing system (more specifically, the treatment chamber) is used to mix/disperse particulates into one or more formulations. Specifically, a first formulation is delivered (e.g., by the pumps described above) via conduits to the inlet end (FIGS. 1 and 2) or to one or more inlet ports formed in the treatment chamber housing (FIG. 3). The first formulation can be any suitable basic buffer system known in the art. For example, the first formulation may comprise sodium bicarbonate, potassium hydroxide, sodium hydroxide, ammonium hydroxide, sodium carbonate, or combinations thereof.

Generally, from about 0.1 grams per minute to about 100,000 grams per minute of the first formulation is typically delivered into the treatment chamber housing. More suitably, the amount of formulation delivered into the treatment chamber housing is from about 1 gram per minute to about 10,000 grams per minute. In the preferred embodiment, the first formulation comprises aqueous sodium bicarbonate with a concentration of from about 0.01 M to about 0.6 M. More preferably, the first formulation comprises aqueous sodium bicarbonate having a concentration of 0.4 M.

With the ultrasonic horn turned on, the first formulation is pumped through a conduit to the inlet end (FIGS. 1 and 2) or to an inlet port disposed on the treatment chamber housing (FIG. 3). In one embodiment, as shown in FIGS. 1 and 2, the first formulation is pumped through the inlet end of the treatment chamber housing. The conduit through which the first formulation is delivered may be moved up and down during delivery to assure composition uniformity in the treatment chamber. In another embodiment, as shown in FIG. 3, the first formulation is continuously pumped through a conduit to an inlet port disposed at the inlet end 325 (a lower end in the orientation of the illustrated embodiment in FIG. 3) at a flow rate to maintain the required concentration of the first formulation within the treatment chamber.

Additionally, the method includes delivering a second formulation, such as those described above, to the interior space of the chamber. In one embodiment, as shown in FIGS. 1 and 2, the second formulation is placed into the interior of the chamber prior to the first formulation being delivered to the chamber. In another embodiment, the second formulation is continuously pumped through a conduit to an inlet port 358 disposed at the inlet end 325 (a lower end in the orientation of the illustrated embodiment in FIG. 3) at a flow rate to maintain the required concentration of the first formulation within the treatment chamber. In this particular embodiment, the second formulation is delivered to the chamber at a rate of from about 0.0001 L/min to about 100 L/min. Preferably, the second formulation is delivered at a rate of from about 0.001 L/min to about 0.100 L/min.

In accordance with the above embodiments, as the formulation and particulates flow downward (as in FIGS. 1 and 2) or upward (as in FIG. 3) within the chamber, the waveguide assembly, and more particularly the horn assembly, is driven by the drive system to vibrate at a predetermined ultrasonic frequency. In response to ultrasonic excitation of the horn, the agitating members that extend outward from the outer surface of the horn dynamically flex/bend relative to the horn, or displace transversely (depending on the longitudinal position of the agitating member relative to the nodal region of the horn).

The formulations and particulates continuously flow longitudinally along the flow path between the horn assembly and the inner surface of the housing sidewall so that the ultrasonic vibration and the dynamic motion of the agitating members cause cavitation in the formulation to further facilitate agitation. The baffle members disrupt the longitudinal flow of formulation along the inner surface of the housing sidewall and repeatedly direct the flow transversely inward to flow over the vibrating agitating members.

As the mixed particulate-containing formulation flows longitudinally past the terminal end of the waveguide assembly, an initial back mixing of the particulate-containing formulation also occurs as a result of the dynamic motion of the agitating member at or adjacent the terminal end of the horn.

Further, downstream flow of the particulate-containing formulation, as in FIGS. 1 and 2, results in the agitated formulation providing a more uniform mixture of components (e.g., components of formulation and particulates) prior to exiting the treatment chamber via the outlet port. Further, by utilizing ultrasonic energy created by the ultrasonic horn described above, agglomeration of particles within the treatment chamber is significantly reduced, and thus, a more fine and homogenous powder may be produced upon isolation. In addition, it has been found that by utilizing ultrasonic energy during the mixing of the first and second formulations described above, a metal-modified particle may be formed that is capable of removing odorous compounds via chemical absorption.

In one embodiment, as illustrated in FIG. 2 and FIG. 3, as the particulate-containing formulation travels through the chamber, a portion of the first and second formulations are directed out of the housing prematurely through the liquid recycle loop as described above. This portion of the first and second formulations is then delivered back into the intake zone of the interior space of the housing of the treatment chamber to be mixed with fresh formulation and particulates. By recycling a portion of the first and second formulations, a more thorough mixing of the formulations and particulates occurs.

Once the particulate-containing formulation is thoroughly mixed, the particulate-containing formulation exits the treatment chamber via the outlet port. In one embodiment, once exited, the particulate-containing formulation can be directed to a post-processing delivery system to be delivered to one or more packaging units where it may be used directly for spraying onto a material substrate or in a dip and squeeze process.

In another embodiment, the metal-modified particles may be recovered, or isolated, from the formulation by filtration and subsequently washed. For example, a fritted glass filter may be used where the pore size of the frit is smaller than the particulate size in diameter, length, or width, and this filter is attached to a filter flask. The particulate containing formulation is transferred to the filter, and a vacuum is applied via a connection to the filter flask. The liquid component of the particulate containing formulation is pulled through the fritted filter and separated from the particles. The particulates are washed with water, and the same mechanism is used to isolate the particulates from the wash liquid.

In a further embodiment, where isolated metal-modified particles are desired for dry-condition applications, the aqueous solvent is removed en vacuo and the isolated particles are washed and dried. For example, a rotovapor instrument, such as a Buchi Rotavapor R-114 from Buchi Labortechnik AG (Flawil, Switzerland), may be used to evaporate the liquid from the particulate containing formulation using applied heat and vacuum. The remaining particulate is collected and washed with water using a fritted filter attached to a flask. Further, the particulate-containing formulation exiting the treatment chamber may be directly filtered to collect the isolated metal-modified particles and then washed and air-dried.

The present disclosure is illustrated by the following examples which are merely for the purpose of illustration and are not to be regarded as limiting the scope of the disclosure or manner in which it may be practiced.

Headspace Gas Chromatography for Quantitative Analysis of Ethyl Mercaptan Removal Quantitative analysis of odor adsorption was determined as described in the Examples described below using Headspace Gas Chromatography. The analyses were conducted on an Agilent Technologies 5890, Series II gas chromatograph with an Agilent Technology 7694 headspace sampler obtained from Agilent Technologies, Waldbronn, Germany. Helium was used as the carrier gas with an injection port pressure of 12.7 psig, a headspace vial pressure of 15.8 psig, and a supply line pressure of 60 psig. A DB-624 column having a length of 30 meters and an internal diameter of 0.25 millimeters was used for the odorous compound. Such a column is available from J&W Scientific, Inc. of Folsom, Calif. The operating parameters used for the headspace gas chromatography are shown below in Table 1.

TABLE 1

| | | |
|---|---|---|
| Zone Temps, ° C. | Oven | 37 |
| | Loop | 42 |
| | TR. Line | 47 |
| Event Time, minutes | GC Cycle time | 10.0 |
| | Vial eq. Time | 10.0 |
| | Pressurized Time | 0.20 |
| | Loop fill time | 0.20 |
| | Loop eq. Time | 0.15 |
| | Inject time | 0.30 |
| Vial Parameters | First vial | 1 |
| | Last vial | 1 |
| | Shake | [off] |

To test a sample, from about 3 mg to about 10 mg of the sample powder was placed in a 20 cubic centimeter headspace vial. Using a syringe, an aliquot of the odorous compound, methyl mercaptan, was transferred to the side wall in the vial. The volume of ethyl mercaptan ranged from about 839 micrograms (about 1 microliter) to about 3356 micrograms (about 4 microliters). Each test sample was analyzed in triplicate.

After transfer of ethyl mercaptan to a test vial, the test vial was immediately sealed with a cap and a septum and placed in the headspace gas chromatography oven at 37° C. After a set equilibrium time of approximately 10 to 23 minutes, a hollow needle was inserted through the septum and into the vial. A one cubic centimeter sample of the headspace, or the air inside the vial, was then injected into the gas chromatograph.

Initially, a control vial with only the aliquot of ethyl mercaptan was tested to define 0% odorous compound adsorption. To calculate the amount of headspace odorous compound removed by each sample, the peak area for the ethyl mercaptan from the vial with the sample was compared to the peak area from the ethyl mercaptan control vial.

EXAMPLE 1

In this Example, various types of silica particles were mixed with copper chloride dihydrate dissolved in aqueous sodium bicarbonate with and without the presence of ultrasonic energy to form metal-modified silica particles. The chemical mechanisms by which the metal-modified silica particles remove odorous compounds were compared.

Three different samples were prepared using SNOWTEX-OXS®, SNOWTEX-C®, and SNOWTEX-PSSO® at 5% wt/wt in an aqueous suspension. Initially, a 100 mL SNOWTEX-OXS® suspension was added to the ultrasonic chamber comprising the horn, agitating members, and baffle system described above in detail. 8.92 grams of copper chloride dihydrate was dissolved in 700 mL of water, and this solution was added to the ultrasonic chamber. The ultrasonic mixing system was then ultrasonically activated using the ultrasonic drive system at 2.4 kW. 6.05 grams of sodium bicarbonate was slowly added to the top of the ultrasonic mixing system. The mole ratio of copper (II) chloride dihydrate to the silica particles was about 50:1, and the final concentration of sodium bicarbonate in the reaction suspension was about 0.04M.

This process was repeated for each of SNOWTEX-C® and SNOWTEX-PSSO®. In these two processes, however, the sodium bicarbonate was added to the ultrasonic mixing system at the bottom of the chamber. Agglomeration and gelation were not observed for the processes utilizing SNOWTEX-C® and SNOWTEX-PSSO®. Agglomeration was observed, however, for the process utilizing SNOWTEX-OXS®.

Ethyl mercaptan (EtSH) removal assessment was carried out using headspace GC techniques, described in more detail below (See Example 4). Specifically, powder samples of CuOXS synthesized with and without ultrasound energy by the methods described above were isolated via rotovap and washed with an excessive amount of water. Approximately 10 mg of powder samples were placed in sample vials, followed by the injection of 4 microliters of neat EtSH. The sample vials were immediately sealed and data collection commenced appropriately using established protocols described above.

Figure 4:
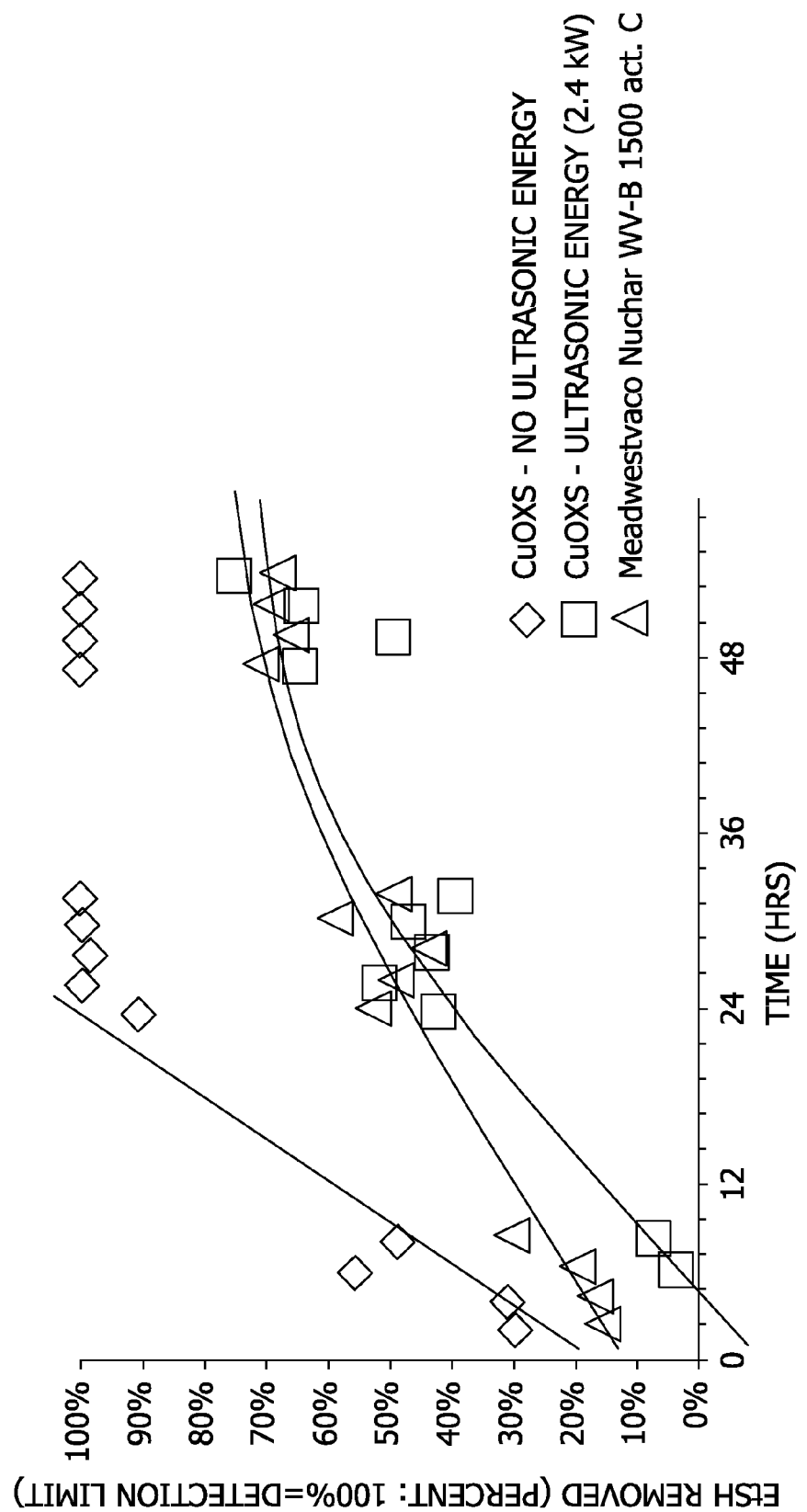

The data directed to the CuOXS preparation without the use of ultrasound showed increasing removal efficacy over time, which suggests a catalytic mechanism for removal of EtSH. The data directed to the CuOXS preparation with the use of ultrasound, however, showed that the removal of EtSH by the ultrasonically prepared metal-modified silica particles was stable over time. More specifically, this data suggests that there was a finite chemical absorption over time, i.e., a saturation point may have been reached. As such, this data illustrates that chemical absorption is the odor removal mechanism for metal-modified silica particles prepared using ultrasonic energy. Chemical absorption is preferred over catalysis, as chemical absorption involves the chemical binding of the odor compound to the odor removal compound, and thus, as opposed to catalysis, is irreversible when subject to physical challenges such as temperature and humidity. These results are illustrated in FIG. 4.

EXAMPLE 2

In this Example, metal-modified silica particles were prepared without the presence of ultrasonic energy. Specifically, a 5% wt/wt modified silica suspension was prepared by mixing a 10% wt/wt silica suspension, a copper (II) chloride dihydrate solution, a sodium bicarbonate solution, and water at the appropriate concentrations and volumes in a beaker. The mole ratio of copper (II) chloride dihydrate to silica particles was about 50:1, and the final concentration of sodium bicarbonate in the reaction suspension was about 0.04M. The volume of the reaction suspension was one liter. The silica suspension was obtained from Nissan Chemical America Corporation of Houston, Tex. under the tradename SNOWTEX-OXS®, the copper (II) chloride dihydrate solution was obtained from Aldrich Chemical, and the sodium bicarbonate solution was obtained from Aldrich Chemical.

Specifically, the copper (II) chloride dihydrate solution was added to the silica suspension as the silica suspension was vigorously stirred using a magnetic stir bar. The sodium bicarbonate solution was then slowly added at a rate of approximately 5 mL/min to the copper (II) chloride dihydrate solution and silica suspension. The final formulation contained 5% wt/wt silica, a 50:1 ratio of copper ions to silica particles, and 0.04M (aq) sodium bicarbonate.

Isolation of solid copper modified silica particles was achieved by removal of water en vacuo, followed by a wash with water and air filtration. Specifically, a rotovapor instrument was used to evaporate the liquid from the particulate containing formulation using applied heat and vacuum. The remaining particulate was controlled and washed with water using a fritted filter attached to a filter flask.

EXAMPLE 3

This Example demonstrated the ability to form copper modified silica nanoparticles using ultrasonic energy. Specifically, the process as described above in Example 2 was carried out in an ultrasonic chamber of an ultrasonic mixing system, as is described above in detail. The ultrasonic mixing system was ultrasonically activated using the ultrasonic drive system at 2.4 kW prior to the addition of the sodium bicarbonate solution. When the reaction temperature inside the ultrasonic mixing system reached a temperature of 180° F., the ultrasonic drive system was reduced to an output of 1.8 kW and remained constant through the remainder of the reaction. The particles were then isolated in the same manner as described in Example 2.

EXAMPLE 4

This Example demonstrated the effectiveness of copper modified silica nanoparticles to remediate ethyl mercaptan. The modified silica particles of Example 2 and Example 3 were tested for ethyl mercaptan remediation using Headspace Gas Chromatography, as is described in more detail below. In addition, activated carbon obtained from Meadwestvaco of Glenn Allen, Va. was tested for comparison. Measurement was recorded approximately 25 minutes after introduction of ethyl mercaptan into a sample vial containing either the modified silica particles of Example 2, the modified silica particles of Example 3, or the activated carbon. The results are shown below in Table 2.

TABLE 2

| Sample | mg ethyl mercaptan/g test sample |
| --- | --- |
| CuOXS-no ultrasonic | 779.3 |
| CuOXS-ultrasonic | 300.3 |
| Activated carbon | 440.6 |

As shown in Table 2, the highest amount of ethyl mercaptan per gram of test sample was removed by the CuOXS particles of Example 2, wherein no ultrasonic energy was present. This data demonstrates that application of ultrasonic energy during the preparation of metal-modified silica particles does not interfere with the ability of the metal-modified silica particles' ability to remediate ethyl mercaptan.

EXAMPLE 5

Figure 5:
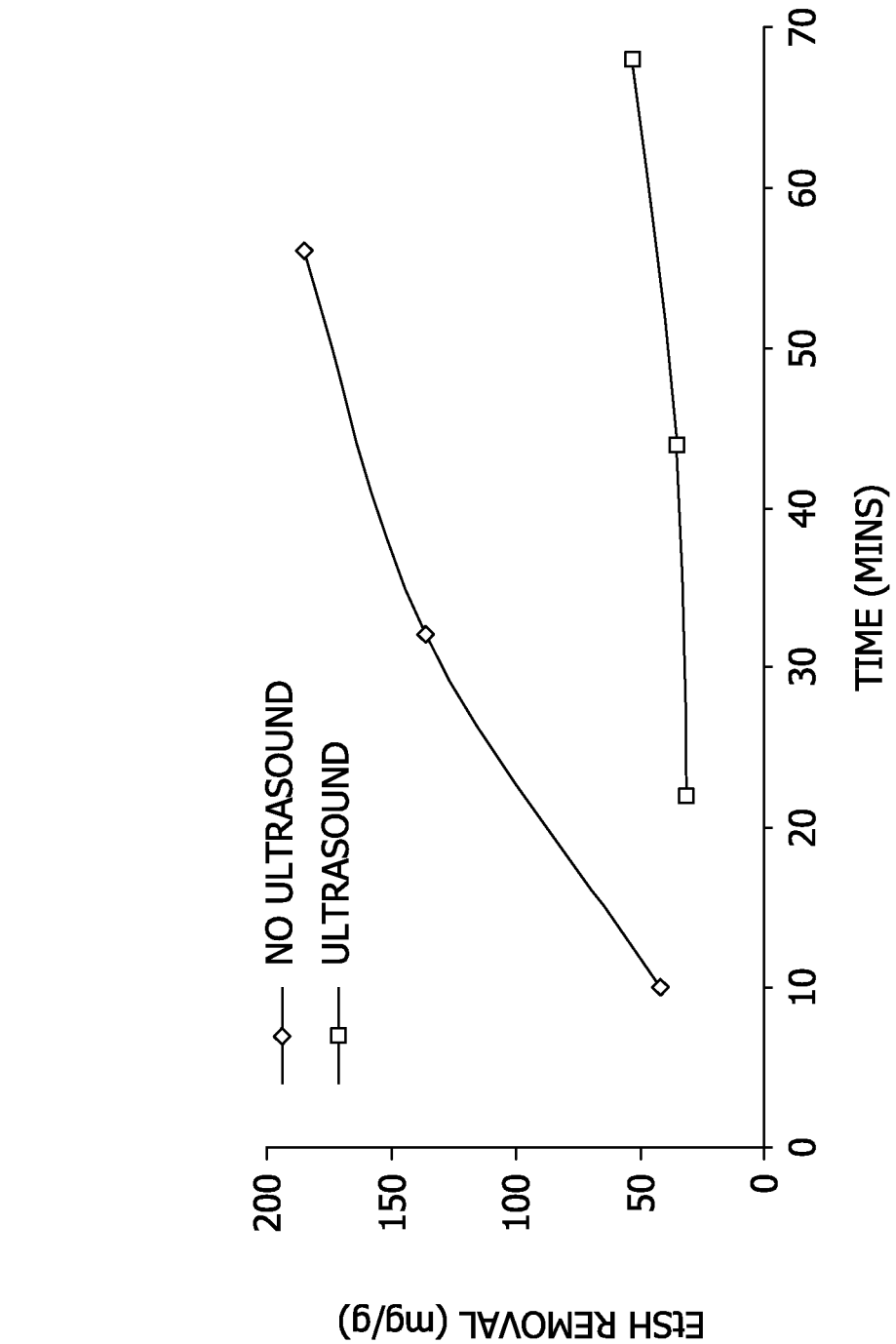

This Example demonstrated the effectiveness of copper modified silica nanoparticles to remediate ethyl mercaptan over a period of time. The modified silica particles of Example 2 and Example 3 were tested for ethyl mercaptan remediation using Headspace Gas Chromatography, as is described in more detail below. In addition, activated carbon obtained from Meadwestvaco of Glenn Allen, Va. was tested for comparison. Measurements were recorded over a 50 hour time period after introduction of ethyl mercaptan into a sample vial containing either the modified silica particles of Example 2, the modified silica particles of Example 3, or the activated carbon. The results are shown in FIG. 5.

From these results, it can be seen that the metal-modified silica particles remove odorous compounds via a catalytic mechanism when the modified particles are prepared without the presence of ultrasonic energy, as the performance of these particles increases over time until the saturation point of the instrument is reached. The removal of odorous compounds by metal-modified silica particles prepared in the presence of ultrasonic energy, however, appears to level off before reaching the detection limit. The plateau-effect of the particles prepared in the presence of ultrasonic energy suggests that the saturation of contact points for the odor compound to bind has been reached.

EXAMPLE 6

Distinct mechanisms by which copper modified silica particles prepared with and without ultrasonic energy remediate ethyl mercaptan, respectively, were demonstrated. The modified silica particles of Example 2 and Example 3 were tested for ethyl mercaptan remediation as described using Headspace Gas Chromatography with variable temperature over time. The GC oven was programmed from 30° C.-250° C. (held at 30° C. for 5 minutes, then ramped to 250° C. at 15° C./min, held at 250° C. for 4 minutes). In addition, activated carbon (obtained from Meadwestvaco of Glenn Allen, Va.) was tested for comparison purpose. Measurement was recorded approximately 3 hours after introduction of ethyl mercaptan into the sample vial. The results are shown in FIG. 6 in terms of peak area (arbitrary units) and retention time. The peak at approximately 3.5 minutes represents EtSH, while the peak at approximately 13.5 minutes represents the disulfide derivative (EtSSEt) of EtSH.

EXAMPLE 7

Figure 7A:
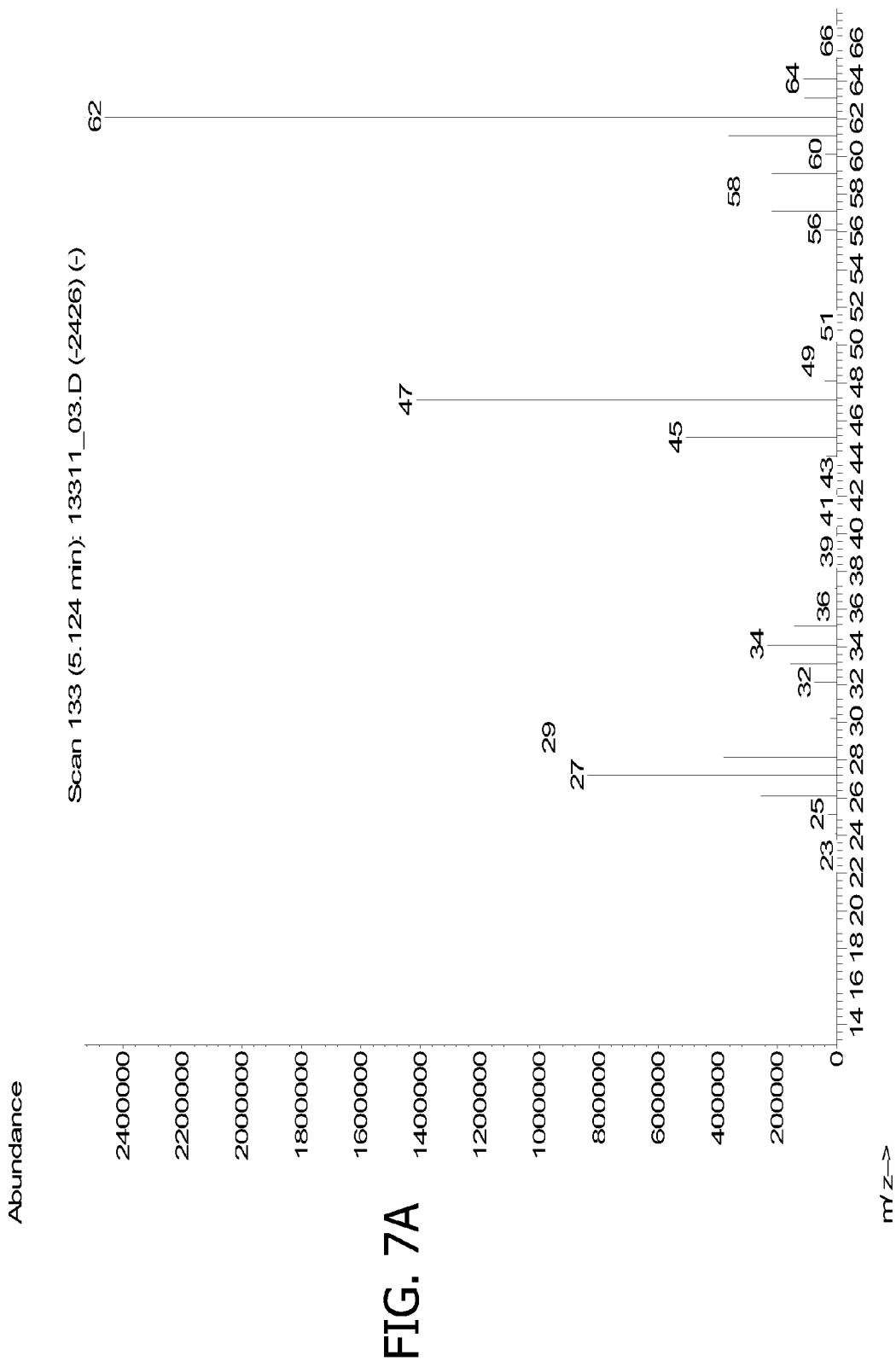
Figure 7B:
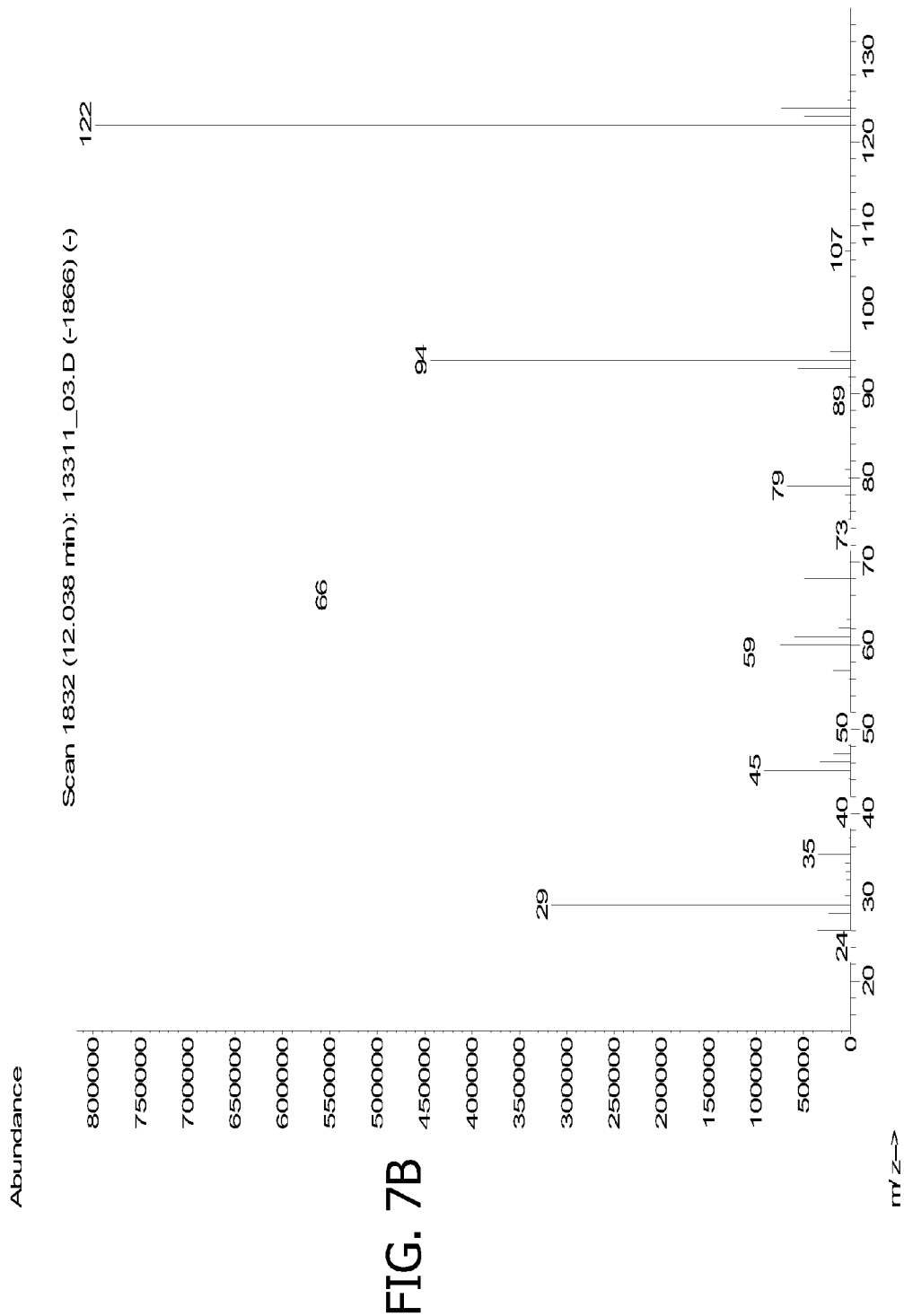

Identification of the disulfide derivative conversion product by the modified silica particles from Example 2 was demonstrated. The modified silica particles from Example 2 and Example 3 assessed for ethyl mercaptan remediation using headspace gas chromatography coupled with mass spectroscopy. An Agilent Technologies 5973N GC/MS with a 6890 gas chromatograph was used to analyze the samples. The samples were analyzed on a J&W DB-5MS capillary column (60 m×0.25 mm×0.25 u film) using split injection (100:1 split at 225° C.). The GC oven was programmed from 50° C. (held for 2 minutes) to 300° C. at 25° C./min. Mass spectra were acquired with ionization energy of 70 eV scanning from 35-250 Da at 3.39 spectra/second. Data was collected and analyzed with ChemStation software supplied with the instrument. The 20 ml headspace vials were sealed with PTFE/Silicone/PTFE septa, and the gas samples collected with a 25 μl Valco Precision Series A-2 sampling syringe. The results are shown in FIGS. 7A and 7B in terms of mass-to charge ratio (M/Z). The mass spectrum (A) corresponds to the GC peak at approximately 3.5 minutes (r.t.) and exhibits an M/Z 62, which is identified as ethyl mercaptan. The mass spectrum (B) corresponds to the GC peak at approximately 13.5 minutes (r.t.) and exhibits an M/Z 122, which is identified as diethyl disulfide.

EXAMPLE 8

Figure 8A:
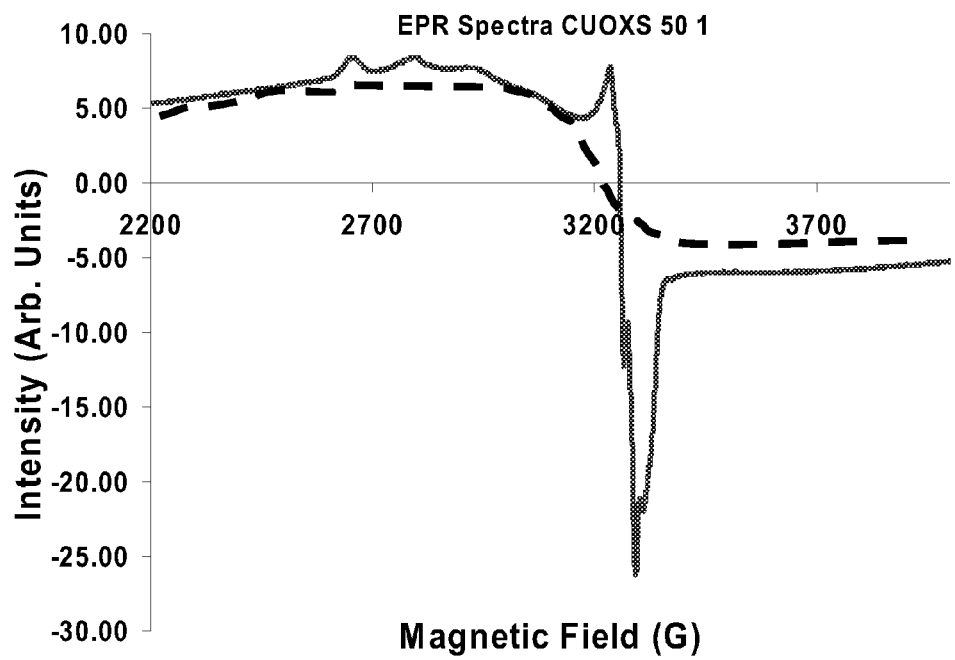
Figure 8B:
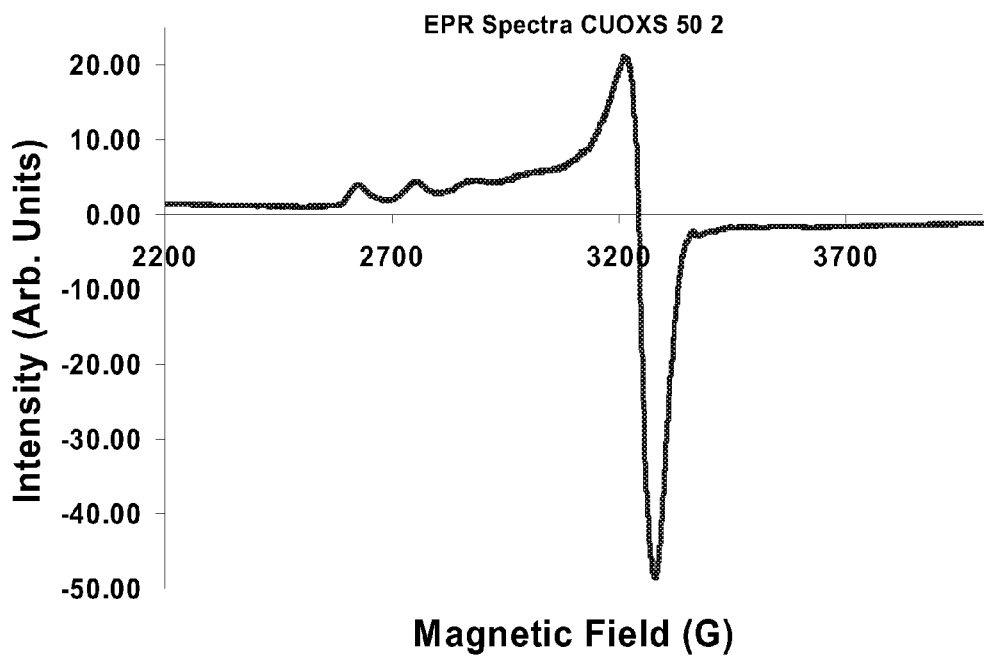

Identification of two distinct copper species on copper-modified silica particles from Example 2 and Example 3, respectively, was demonstrated. Electron paramagnetic resonance (EPR) spectroscopy was used to identify the nature of the copper species on copper-modified silica particles from Example 2 and Example 3. The EPR spectrum A in FIG. 8A corresponds to copper-modified silica particles from Example 2; the asymmetric spectrum suggests the presence of both isolated and clustered copper species. The EPR spectrum B in FIG. 8B corresponds to copper-modified silica particles from Example 3; the relatively symmetric spectrum suggests the presence of predominantly isolated copper species.

EXAMPLE 9

The copper content in copper-modified silica particles in Example 2 and Example 3, respectively, was determined using inductively coupled plasma (ICP) spectrometry. The results are shown in Table 3.

TABLE 3

| Description | Copper content (%) |
|---|---|
| Copper-modified silica particles, Example 2 - a | 2.78 |
| Copper-modified silica particles, Example 2 - b | 2.74 |
| Copper-modified silica particles, Example 2 - c | 2.53 |
| Copper-modified silica particles, Example 3 - a | 2.67 |
| Copper-modified silica particles, Example 3 - b | 2.61 |
| Copper-modified silica particles, Example 3 - c | 2.56 |

EXAMPLE 10

Figure 9A:
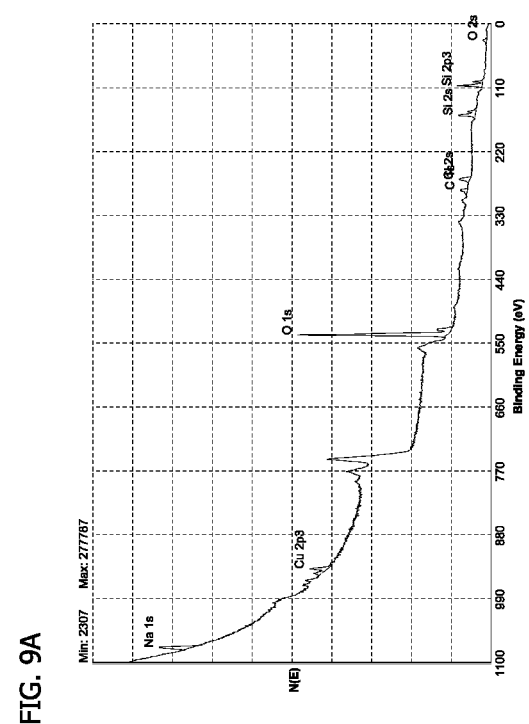
Figure 9B:
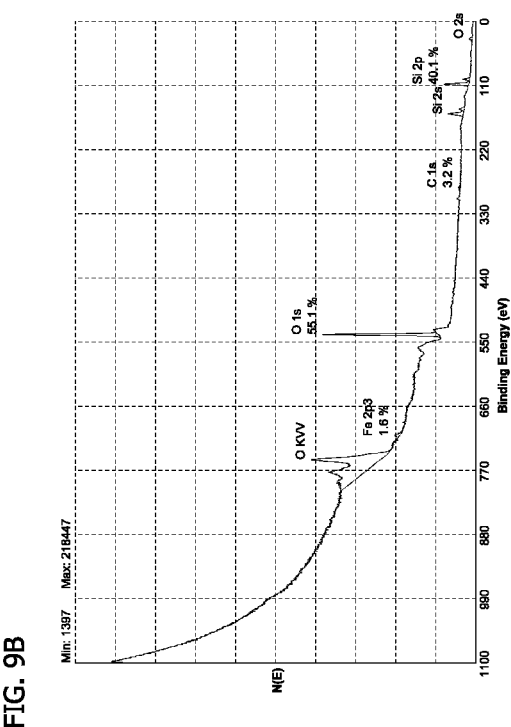

X-ray photoelectron spectroscopy (XPS) was performed on copper modified silica particles from Example 2 (CuOXS-2) and copper modified silica particles from Example 3 (CuOXS-3) for identifying the chemical nature of copper species. XPS spectra are presented in FIG. 9A and FIG. 9B. Each spectrum was shifted to match the adventitious carbon peak (284.8 eV). In both the samples important elements were analyzed for their chemical origin and are tabulated in Table 4.

TABLE 4

| | Sample | | | |
|---|---|---|---|---|
| | CuOXS-1 | | CuOXS-2 | |
| Element | Peak | Chemical origin | Peak | Chemical Origin |
| C | 284.80 | C=O | 284.80 | C—OH |
| | 287.41 | | 286.67 | C=O |
| | | | 287.30 | |
| O | 532.88 | C—O | 532.65 | C—O |
| | 535.33 | C=O | 535.77 | C=O |
| Si | 103.41 | $SiO_2$ | 99.04 | Si |
| | 105.99 | Ga | 99.75 | Si |
| | 98.93 | Si | 103.26 | $SiO_2$ |
| | | | 106.43 | Ga |
| Cu | 935.61 | $CuCl2$ | Cu | No copper peaks were observed |
| | 936.45 | not identified | | |
| | 937.96 | not identified | | |
| | 942.81 | not identified | | |
| | 944.85 | not identified | | |
| | 946.69 | not identified | | |

XPS spectra of CuOXS-1 sample shows several peaks related to copper compounds. However, only one peak could be identified and is related to CuCl2 (from NIST database). CuOXS-2 sample spectra do not have peaks related to copper. The absence of Cu peak in the XPS spectra could be due to some coating on the particles surface. Since XPS probes only few atomic surface layers, copper species coated with some organic/inorganic layer will be difficult to identify using this technique.

EXAMPLE 11

BJH pore size analyses for copper modified silica particles from Example 2 (CuOXS50 1) and copper modified silica particles from Example 3 (CuOXS50 2) showed higher pore volumes for CuOXS50 2. Results are shown in FIG. 10. The area under each curve represents the pore volume for the respective sample.

The data from Examples 6-11 strongly demonstrates the compositional differentiation of copper modified silica particles from Example 2 and Example 3 and how each, respectively, remediates ethyl mercaptan differently. Example 6 and Example 7 are gas chromatography-headspace and gas chromatography-headspace coupled with mass spectrometry experiments. The data shows the conversion of ethyl mercaptan to its disulfide derivative diethyl disulfide by copper modified silica particles from Example 2. This reaction mechanism is, therefore, catalytic in nature; and those skilled in the art should be able to recognize the reaction mechanism applies to odorous compounds with similar redox potential. Examples of such compounds include organic compounds with aldehyde and acid functional groups. For copper modified silica particles from Example 3, the data shows a chemical absorption mechanism with evidence of auto-oxidation of a low concentration of ethyl mercaptan to its disulfide derivative. Those skilled in the art should recognize the tendency of sulfide containing compounds to auto-oxidate under ambient conditions. Additionally, data from Example 6 demonstrates evidence of such auto-oxidation in test samples not containing copper modified silica particles.

Data from Example 8 demonstrates the unique difference in the copper species in copper modified silica particles from Example 2 and Example 3, respectively. The electron paramagnetic spectroscopic (EPR) spectrum for copper modified silica particles from Example 2 is asymmetric, which suggests the nature of the copper species is clustered. The EPR spectrum for copper modified silica particles from Example 3 is more symmetric, which suggests the presence of dominantly isolated copper species. Those skilled in the art should recognize the difference in EPR spectra strongly suggests two unique and different copper species in copper modified silica particles from Example 2 and Example 3.

Example 9 demonstrates the presence of copper in copper modified silica particles from Example 2 and Example 3 at comparable concentration. Data from Example 10 demonstrates that, despite the presence of copper (data from Example 9), the orientation and positioning of copper species on the silica surface in copper modified silica particles from Example 2 and Example 3 are distinct and different.

In Example 10, the nature of the characterization technique analyzes for copper at the top 100 nanometer layer of the material. No presence of copper was detected for copper modified silica particles from Example 3, while copper was detected for copper modified silica particles from Example 2. This difference, combined with data from Example 9 demonstrating the comparable presence of copper in copper modified silica particles from Example 2 and Example 3, strongly suggests the copper species are different, respectively.

Data in Example 11 demonstrates a higher concentration of pore volume in copper modified silica particles from Example 3 compared to Example 2. This data suggests the trigger for the unique composition in copper modified silica particles from Example 3 may be due to a cavitation mechanism enabled by use of ultrasonic energy. The cavitation, thereby, allows for copper to be deposited onto the silica surface in a manner that favors isolated copper species; consequently, this unique composition of copper modified silica particles remediate ethyl mercaptan differently than copper modified silica particles from Example 2.

When introducing elements of the present disclosure or preferred embodiments thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A method for preparing metal-modified particles, the method comprising: providing a treatment chamber comprising: an elongate housing having longitudinally opposite ends and an interior space, the housing being closed at at least one longitudinal end and having at least a first inlet port for receiving a first formulation comprising a basic buffer system, a second inlet port for receiving a second formulation comprising a salt of a transition metal and silica particles into the interior space of the housing, and at least one outlet port through which a metal-modified particulate-containing formulation is exhausted from the housing following ultrasonic mixing of the first and second formulations to form the metal-modified particulate-containing formulation, the outlet port being spaced longitudinally from the first and second inlet ports such that the first and second formulations flow longitudinally within the interior space of the housing from the inlet ports to the outlet port; and an elongate ultrasonic waveguide assembly extending longitudinally within the interior space of the housing and being operable at a predetermined ultrasonic frequency to ultrasonically energize and mix the first and second formulations flowing within the housing, the waveguide assembly comprising an elongate ultrasonic horn disposed at least in part intermediate the first and second inlet ports and the outlet port of the housing and having an outer surface located for contact with the first and second formulations flowing within the housing from the first and second inlet ports to the outlet port, and a plurality of discrete agitating members in contact with and extending transversely outward from the outer surface of the horn intermediate the first and second inlet ports and the outlet port in longitudinally spaced relationship with each other, the agitating members and the horn being constructed and arranged for dynamic motion of the agitating members relative to the horn upon ultrasonic vibration of the horn at the predetermined frequency and to operate in an ultrasonic cavitation mode of the agitating members corresponding to the predetermined frequency and the first and second formulations being mixed in the chamber; delivering the first formulation via the first inlet port into the interior space of the housing; delivering the second formulation via the second inlet port into the interior space of the housing; ultrasonically mixing the first and second formulations via the elongate ultrasonic waveguide assembly operating in the predetermined ultrasonic frequency to imbed the metal ions into the subsurface of the silica particles such that no trace of the imbedded metal ions can be analytically detected on the surface of the silica particles.

2. The method as set forth in claim 1, wherein delivering the first formulation comprises delivering the first formulation via a first delivery system operable to deliver the first formulation to the interior space of the housing of the treatment chamber through the first inlet port, wherein the first formulation is delivered at a rate of from about 0.01 grams per minute to about 100,000 grams per minute.

3. The method as set forth in claim 1, wherein delivering the second formulation comprises delivering the second formulation via a second delivery system operable to deliver the second formulation to the interior space of the housing of the treatment chamber through the second inlet port, wherein the second formulation is delivered at a rate of from about 0.0001 L/min to about 100 L/min.

4. The method as set forth in claim 1, wherein the second formulation is provided to the system in an amount such that the silica particles of the second formulation are present in an amount of at least 4% (by weight of the second formulation).

5. The method as set forth in claim 1, wherein the transition metal is selected from the group consisting of scandium, titanium, vanadium, chromium, manganese, iron, cobalt, nickel, copper, zinc, silver, and gold.

6. The method as set forth in claim 1 further comprising: removing the metal-modified particulate-containing formulation from the ultrasonic mixing system via the outlet port; and isolating the metal-modified particles from the metal-modified particulate-containing formulation.

7. The method as set forth in claim 1 wherein the first formulation is selected from the group consisting of aqueous sodium bicarbonate, potassium hydroxide, sodium hydroxide, ammonium hydroxide, sodium carbonate, and combinations thereof.

8. The method as set forth in claim 1 wherein the elongate ultrasonic waveguide assembly further comprises a baffle assembly disposed within the interior space of the housing and extending at least in part transversely inward from the housing toward the horn to direct the first and second formulations in the housing to flow transversely inward into contact with the agitating members.

9. A method for reducing odor, the method comprising: preparing metal-modified silica particles; isolating the metal-modified silica particles; and contacting the metal-modified silica particles to an odorous compound; wherein preparing metal modified silica particles comprises: providing a treatment chamber comprising: an elongate housing having longitudinally opposite ends and an interior space, the housing being closed at at least one longitudinal end and having at least a first inlet port for receiving a first formulation comprising a basic buffer system, a second inlet port for receiving a second formulation comprising a salt of a transition metal and silica particles into the interior space of the housing, and at least one outlet port through which a metal-modified particulate-containing formulation is exhausted from the housing following ultrasonic mixing of the first and second formulations to form the metal-modified particulate-containing formulation, the outlet port being spaced longitudinally from the first and second inlet ports such that the first and second formulations flow longitudinally within the interior space of the housing from the inlet ports to the outlet port; and an elongate ultrasonic waveguide assembly extending longitudinally within the interior space of the housing and being operable at a predetermined ultrasonic frequency to ultrasonically energize and mix the first and second formulations flowing within the housing, the waveguide assembly comprising an elongate ultrasonic horn disposed at least in part intermediate the first and second inlet ports and the outlet port of the housing and having an outer surface located for contact with the first and second formulations flowing within the housing from the first and second inlet ports to the outlet port, and a plurality of discrete agitating members in contact with and extending transversely outward from the outer surface of the horn intermediate the first and second inlet ports and the outlet port in longitudinally spaced relationship with each other, the agitating members and the horn being constructed and arranged for dynamic motion of the agitating members relative to the horn upon ultrasonic vibration of the horn at the predetermined frequency and to operate in an ultrasonic cavitation mode of the agitating members corresponding to the predetermined frequency and the first and second formulations being mixed in the chamber; delivering the first formulation via the first inlet port into the interior space of the housing; delivering the second formulation via the second inlet port into the interior space of the housing; and ultrasonically mixing the first and second formulations via the elongate ultrasonic waveguide assembly operating in the predetermined ultrasonic frequency to imbed the metal ions into the subsurface of the silica particles such that no trace of the imbedded metal ions can be analytically detected on the surface of the silica particles to form metal-modified silica particles.

10. The method as set forth in claim 9, wherein delivering the first formulation comprises delivering the first formulation via a first delivery system operable to deliver the first formulation to the interior space of the housing of the treatment chamber through the first inlet port, wherein the first formulation is delivered at a rate of from about 0.01 grams per minute to about 100,000 grams per minute.

11. The method as set forth in claim 9, wherein delivering the second formulation comprises delivering the second formulation via a second delivery system operable to deliver the second formulation to the interior space of the housing of the treatment chamber through the second inlet port, wherein the second formulation is delivered at a rate of from about 0.0001 L/min to about 100 L/min.

12. The method as set forth in claim 9, wherein the second formulation is provided to the system in an amount such that the silica particles of the second formulation are present in an amount of at least 4% (by weight of the second formulation).

13. The method as set forth in claim 9, wherein the transition metal is selected from the group consisting of scandium, titanium, vanadium, chromium, manganese, iron, cobalt, nickel, copper, zinc, silver, and gold.

14. The method as set forth in claim 9 wherein the first formulation is selected from the group consisting of aqueous sodium bicarbonate, potassium hydroxide, sodium hydroxide, ammonium hydroxide, sodium carbonate, and combinations thereof.

* * * * *